United States Patent [19]

Rosenberg

[11] Patent Number: 4,538,613
[45] Date of Patent: Sep. 3, 1985

[54] COHERENT BEAM COUPLER SYSTEM

[76] Inventor: Larry Rosenberg, 3440 Caroline Ave., Culver City, Calif. 90230

[21] Appl. No.: 458,740

[22] Filed: Jan. 17, 1983

[51] Int. Cl.$^3$ ............................................. A61N 5/06
[52] U.S. Cl. ...................................... 128/395; 128/6
[58] Field of Search .................................. 128/4–8,
128/303.1, 395, 399, 633, 634, 637, 664, 665;
219/121 LB, 121 LQ, 121 LU, 121 LV;
33/DIG. 21

[56] References Cited

U.S. PATENT DOCUMENTS

| | | | |
|---|---|---|---|
| 3,710,798 | 1/1973 | Bredemeier | 128/303.1 |
| 3,782,823 | 1/1974 | Kantorski et al. | 219/121 LB |
| 3,806,829 | 4/1974 | Dustan et al. | 219/121 LA |
| 3,830,222 | 8/1974 | Chance | 128/665 |
| 3,841,330 | 10/1974 | Storz | 128/4 |
| 3,914,013 | 10/1975 | Rosenberg | 128/303.1 |
| 3,941,121 | 3/1976 | Olinger et al. | 128/6 |
| 4,072,146 | 2/1928 | Howes | 128/348 |
| 4,118,619 | 10/1978 | McArthur et al. | 219/121 LQ |
| 4,146,019 | 3/1979 | Bass et al. | 128/6 |
| 4,170,997 | 10/1979 | Pinnow et al. | 128/4 |
| 4,210,029 | 7/1980 | Porter | 128/634 |
| 4,213,462 | 7/1980 | Sato | 128/634 |
| 4,249,540 | 2/1981 | Koyama et al. | 128/633 |
| 4,266,549 | 5/1981 | Kimura | 128/395 |
| 4,316,467 | 2/1982 | Muckerheide | 128/303.1 |
| 4,321,930 | 3/1982 | Jobsis et al. | 128/633 |
| 4,423,736 | 1/1984 | DeWitt et al. | 128/633 |

FOREIGN PATENT DOCUMENTS 2922511 12/1980 Fed. Rep. of Germany .......... 128/4

Primary Examiner—Edward M. Coven
Assistant Examiner—Max F. Hindenburg
Attorney, Agent, or Firm—Larry Rowan; Malke Leah

[57] ABSTRACT

A system and method for diagnosing and treating undesired internal conditions and structures, such as occluded vessels or aberrant histological regions. Diagnosis is effected by means of doppler analysis of laser light directed to the effected site from an inserted laser-containing unit, and treatment is accomplished by the same unit through direction of laser emissions of controlled characteristics toward the target site, thereby accomplishing departicalization, disintegration, and elimination through normal bodily processes of the undesired structure. Coherent radiation of a determinate size, wave amplitude, and electronic composition is precisely directed to given loci of operation for non-invasive analysis and treatment of aberrant sites. The invention embodies a noval unitary device with an assemblage of automated diaphragms, beam splitters, electronic choppers, an automated dye cell subsystem, and a focusing turret equipped with rotating lens elements and a piezoelectric element. The system directs, focuses, and alters the electronic characteristics of one or more laser emissive sources onto a fiber optics array. The assemblage of subsystems includes an aspiration infusion pump, aspiration conduits, infusion conduits, and emission fiber optics and return self-focusing fiber optics elements within an automated hydraulic hypodermic delivery system.

42 Claims, 23 Drawing Figures

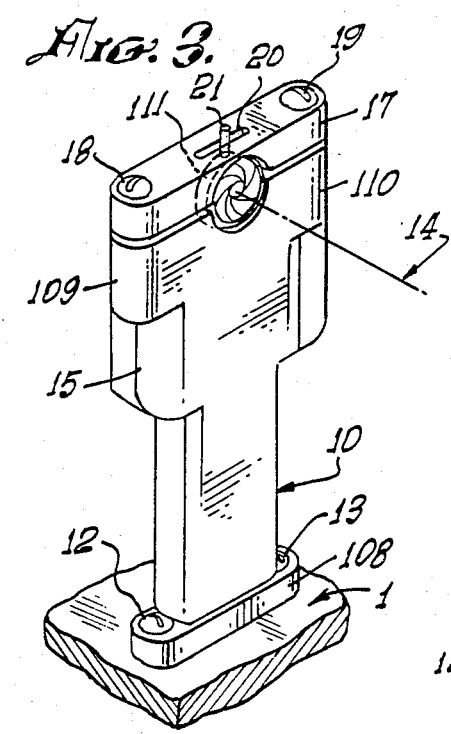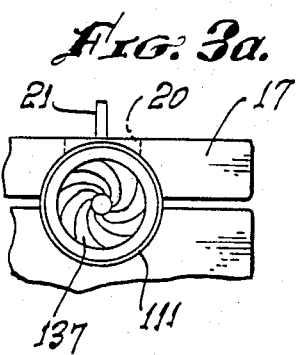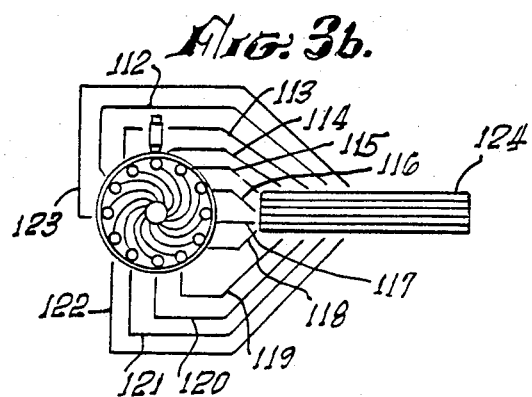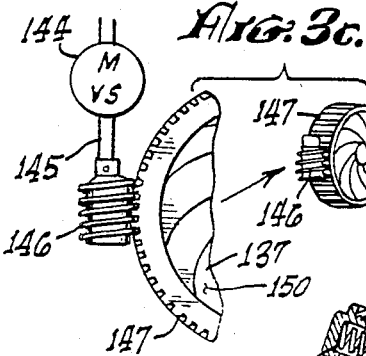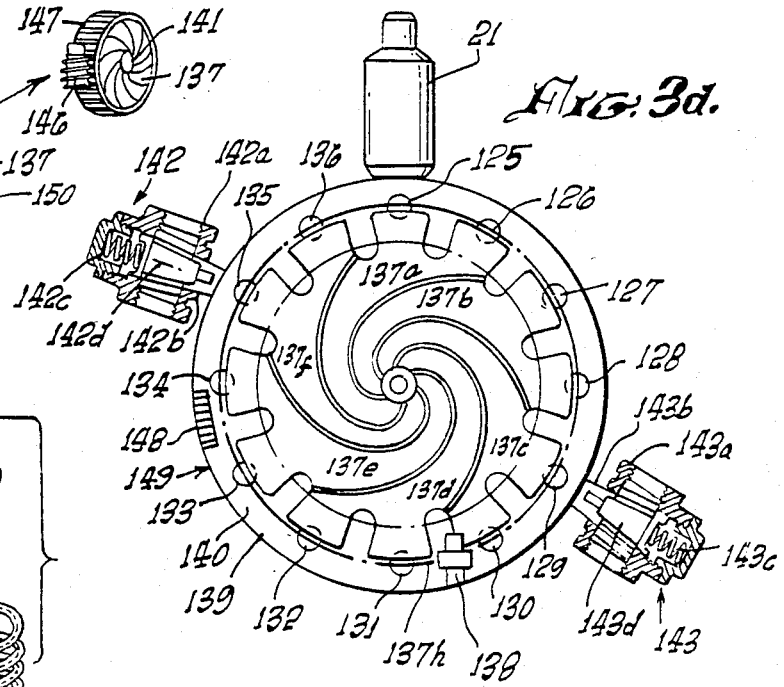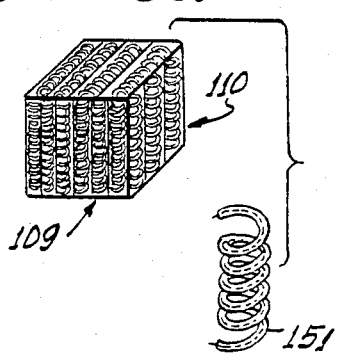

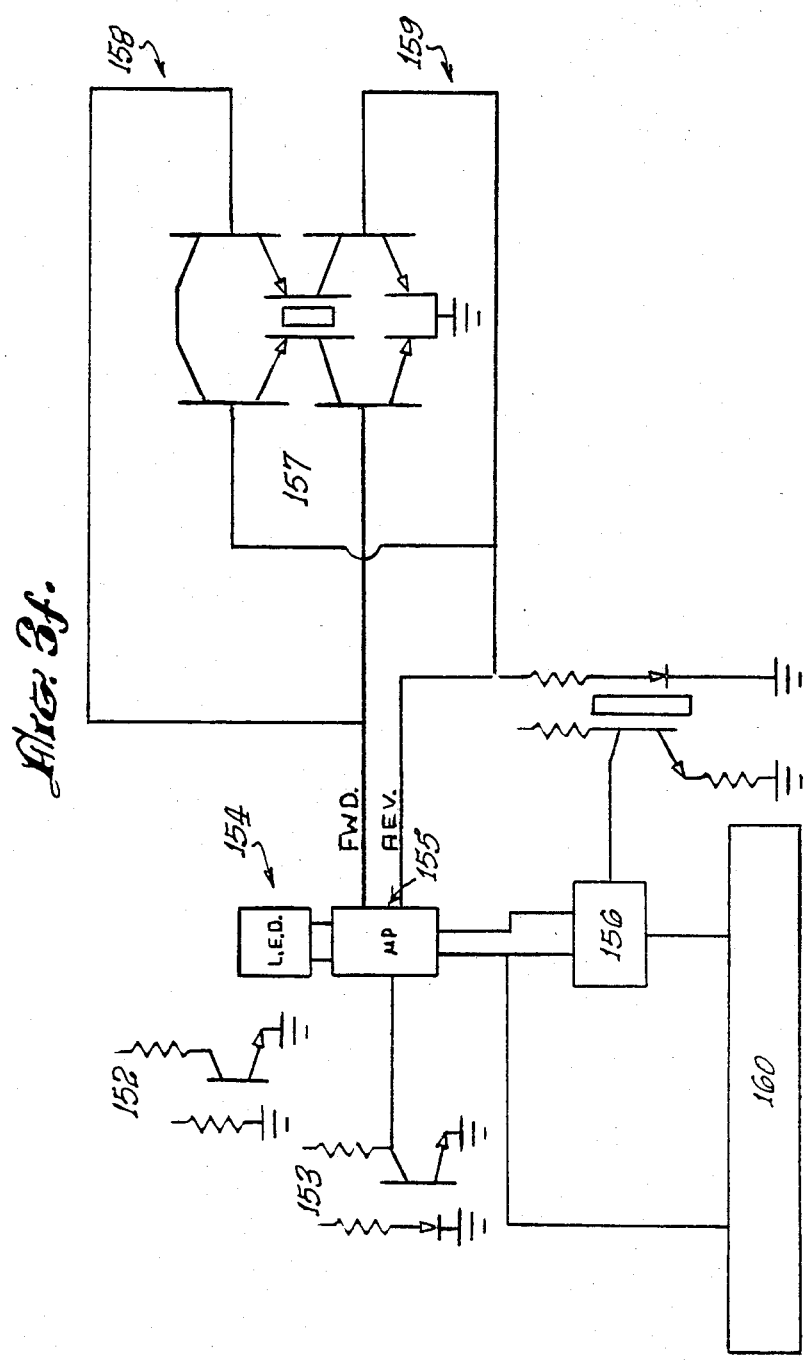

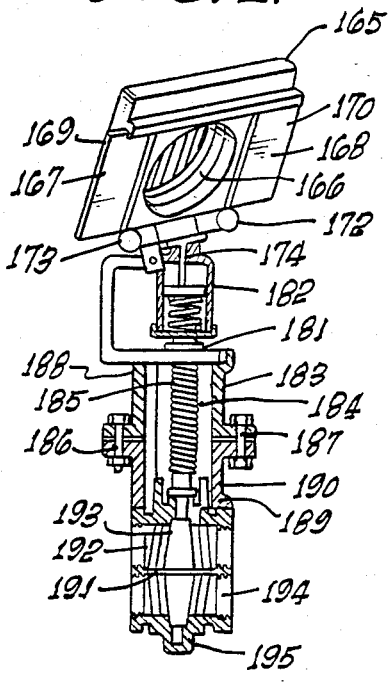
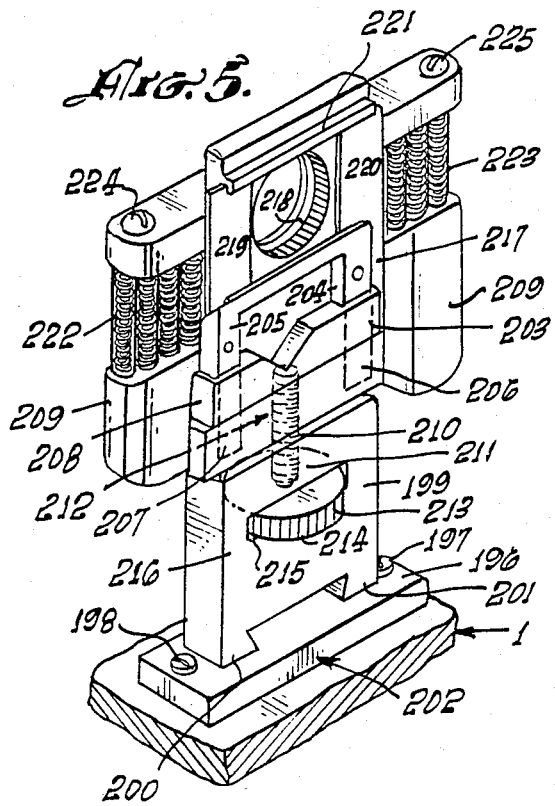
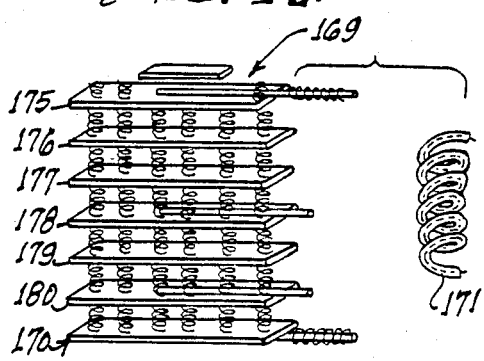
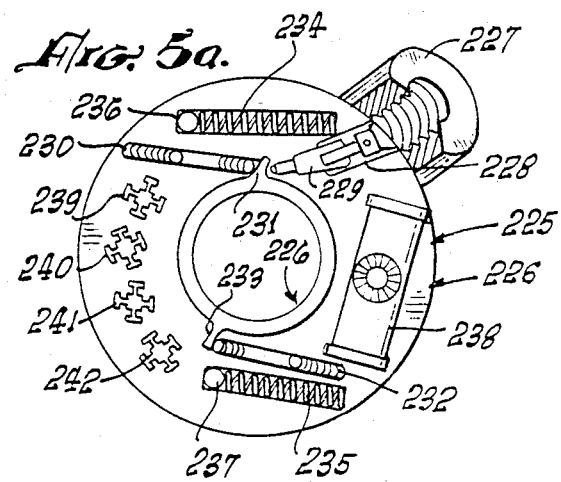
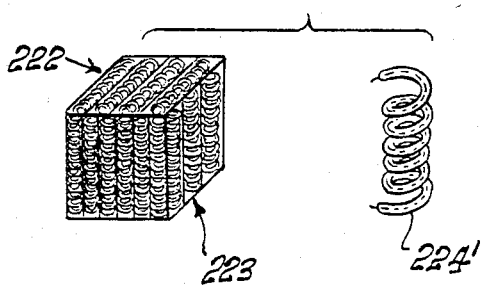

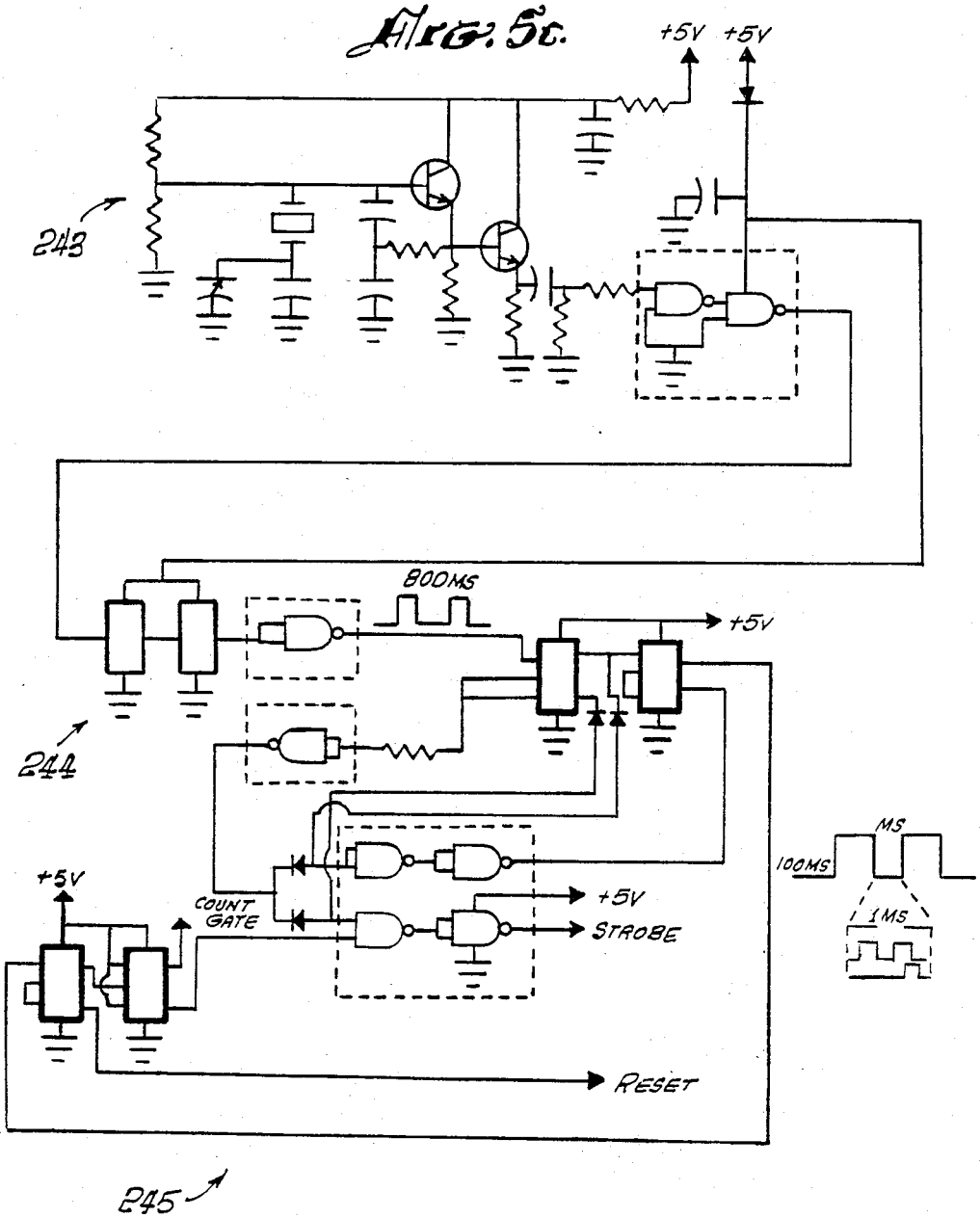

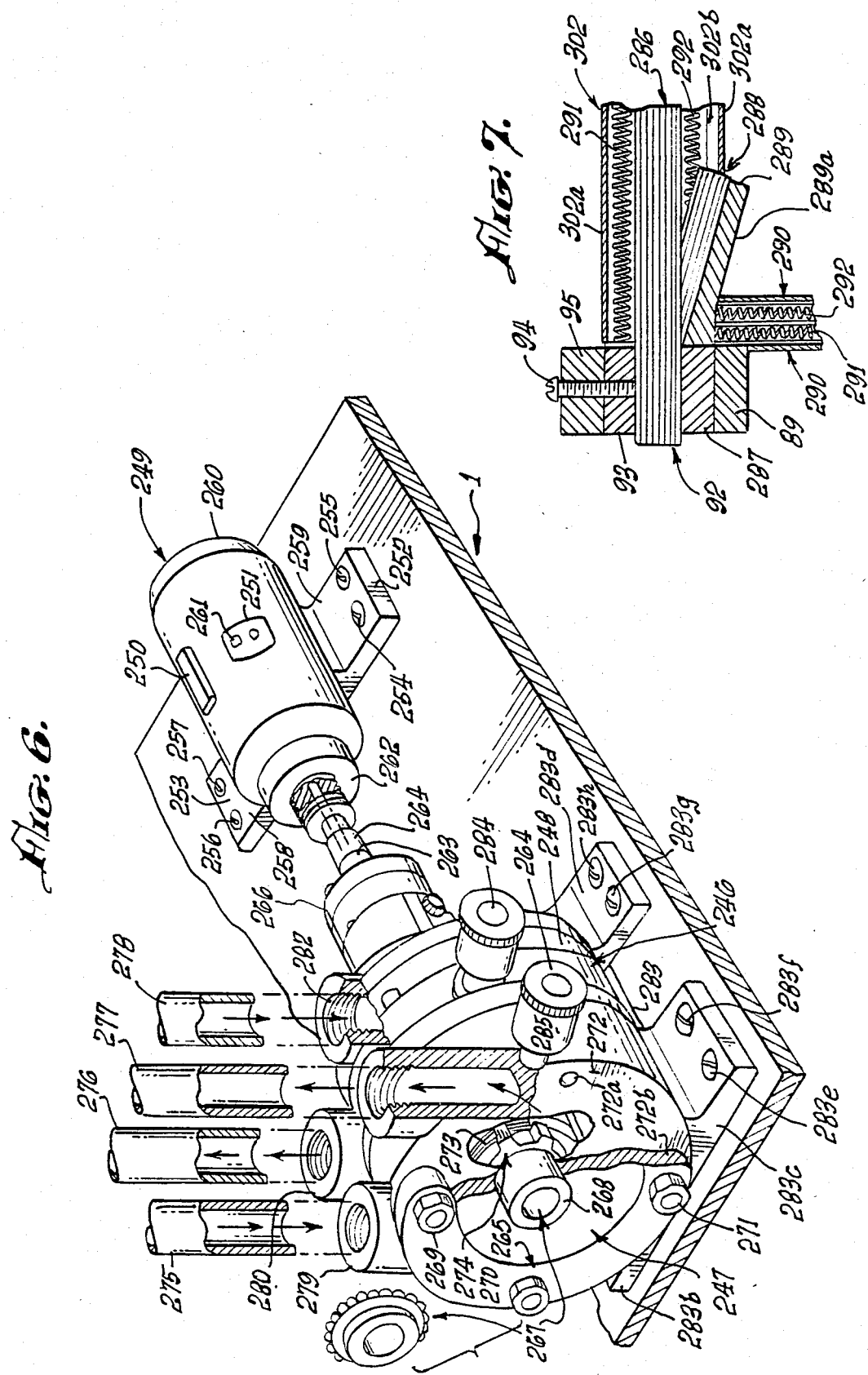

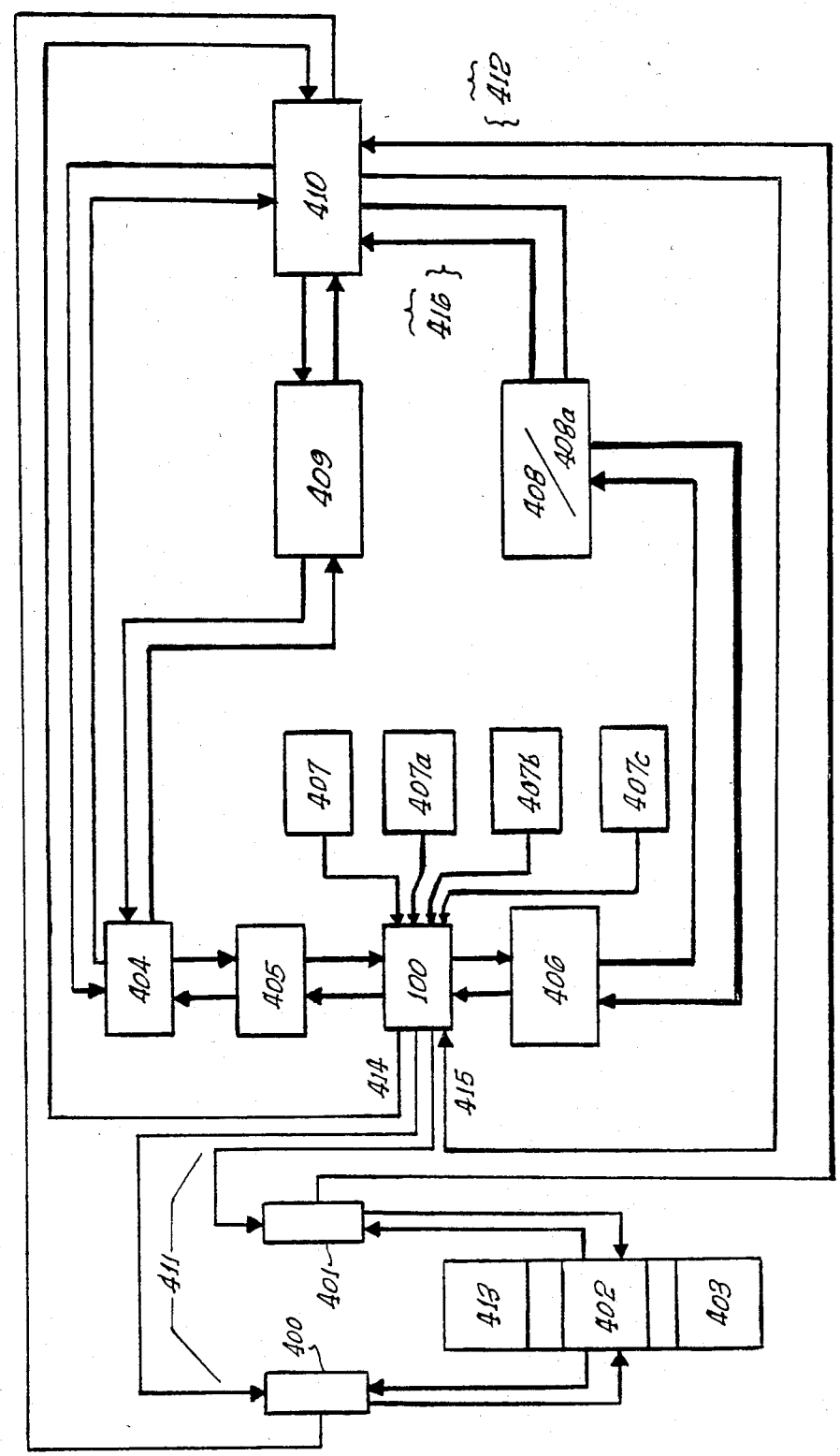

COHERENT BEAM COUPLER SYSTEM

BACKGROUND OF THE INVENTION

1. Field of the Invention

The invention pertains to systems and methods for diagnosis and treatment of aberrant physiological conditions, such as disease, by means of laser light.

2. Description of the Prior Art

Conventional surgical techniques suffer from a number of significant drawbacks, which vary depending upon the extent of involvement, the size of the operative site, propensity toward infection, physical trauma, and shock, among other factors. Thus, in recent years there has been substantial interest in, and development of, alternatives to conventional surgical techniques. Such alternatives include cryogenics electrocoagulation techniques and radio frequency; however, these often produce electroconvulsive or thermal foci in regions surrounding a given target site. Such foci may have serious consequences relative to certain cardiac as well as neurological tissues.

Microwave techniques (excluding masers) and various radioactive emitters are difficult to control with respect to involvement of tissue in regions adjacent a target site. Vasodilation techniques, whereby carbon dioxide is directly administered to a clotted vessel or wherein employment of a catheter is utilized to expand a vessel, exhibit various shortcomings. For example, occlusions dislodged from a vessel by reaming or scraping can relocate to other, more inaccessible sites, as can occlusions dislodged by the introduction of a bolus of carbon dioxide. Circumferential expansion of a catheter inside a vessel, thus forcing the occlusion against the wall of the intima by compression, may result in reaccumulation of plaque on the vessel wall and subsequent reformation of the occlusion in addition to possible fragmenting and relocation of the obstruction and loss in functional integrity of the wall of the vessel; a rupture or blow-out of the vessel may also occur if an embolism is present.

Chemical techniques for dissolving clots or occlusions may be relatively slow-acting and are often complicated by side effects, such as electrolyte imbalance or neurological dysfunctions. Side effects of obstruction of a thrombus through various washing techniques in connection with the introduction of chemical agents may create long-term side effects depending on the size of dosage and tolerance level of the patient.

Alternative techniques and equipment utilizing laser light have been developed in recent years. Examples of such existing systems are represented by U.S. Pat. No. 3,914,013, Coherent Radiation Beam Coupler, issued to the inventor hereof. Existing apparatus employing laser light for purposes of accomplishing surgery does not provide for wholly effective utilization of the potential of laser light for diagnosis and surgery in that such apparatus may exhibit characteristics of excessive complexity or bulkiness and lacks provision for effective diagnosis in addition to treatment of aberrant conditions.

Thus, there has been a felt but unfulfilled need for diagnosing and treating by means of laser light aberrant physiological structures and conditions, particularly internally of the body.

SUMMARY OF THE INVENTION

An improved coherent beam coupler adapted to diagnosing and treating aberrant physiological structures and conditions comprises means for insertion into the body adjacent sites of suspected or known aberrant conditions or structures. Means are provided for supplying laser light input to and receiving laser light output from the insertion means for purposes of accomplishing doppler analysis of laser light emitted by the insertion means in the body, reflected off or re-emitted from the aberrant site, and transmitted from the insertion means for doppler analysis. Apparatus is provided for conducting such doppler analysis of wavelength, electronic composition intensity and the like in the light reflected and/or emitted from the aberrant site for purposes of determining characteristics of such aberrant site. Laser light is supplied to the insertion means for purposes of treating the aberrant site through departicalization thereof as a result of direction thereupon of laser light. Electronic optical systems for directing and controlling such laser light are provided, together with computer controls thereof. Such electronic optical systems including a diaphragm, beam splitters, electronic choppers, dye cell means, and a focusing turret member. The insertion means includes a hypodermic member, together with aspiration and infusion pump means and conduit means, and fiber optic means. A method in accordance with the invention provides for emission of laser light toward, and reflection of such light from, suspected aberrant physiological sites and analysis of the changed characteristics of such reflected light for purposes of diagnosing the aberrant condition or structure. In accordance with the method, the laser light is then directed to the aberrant site for treatment thereof through departicalization in accordance with the diagnosis.

BRIEF DESCRIPTION OF THE DRAWINGS

FIG. 3 is a detailed perspective view of a diaphragm included in the system of FIG. 2;

FIG. 3a is an enlarged detail view of a portion of the diaphragm of FIG. 3;

FIG. 3b is a fragmentary view of a subassembly of the diaphragm of FIG. 3;

FIG. 3c is a detail view of a gear assembly for the diaphragm depicted in FIG. 3;

FIG. 3d is a detail perspective view of the diaphragm of FIG. 3;

FIG. 3e is a detail view of thermal units utilized for dissipation of heat relative to the structure depicted in FIG. 3;

FIG. 3f is a highly simplified schematic diagram of one optical encoding/optical interrupt assembly employed in connection with the diaphragm of FIG. 3;

FIG. 4 is a detailed cross-sectional view of one beam splitter unit utilized in connection with the invention;

FIG. 4a is an enlarged detail view of thermal dissipation units employed in connection with the beam splitter unit of FIG. 4;

FIG. 5 is a detailed sectional view of a shutter housing employed in connection with the invention;

FIG. 5a is a cross-sectional view of the modified shutter means of FIG. 5, taken along the central axis;

FIG. 5b is a detail view of heat exchanger and heat dissipation units employed in connection with the shutter of FIG. 5;

FIG. 5c is a schematic representation of one auxiliary timing circuit employed in connection with the shutter of FIG. 5;

FIG. 6 is a detail view of a pump and motor assembly employed in connection with the invention;

FIG. 7 is a cross-sectional view of fiber optic bundles and associated elements, taken along the central axis;

FIG. 10 is a simplified block diagram and schematic representation of the improved coherent beam coupler in connection with associated apparatus.

DETAILED DESCRIPTION OF THE INVENTION

Figure 1:
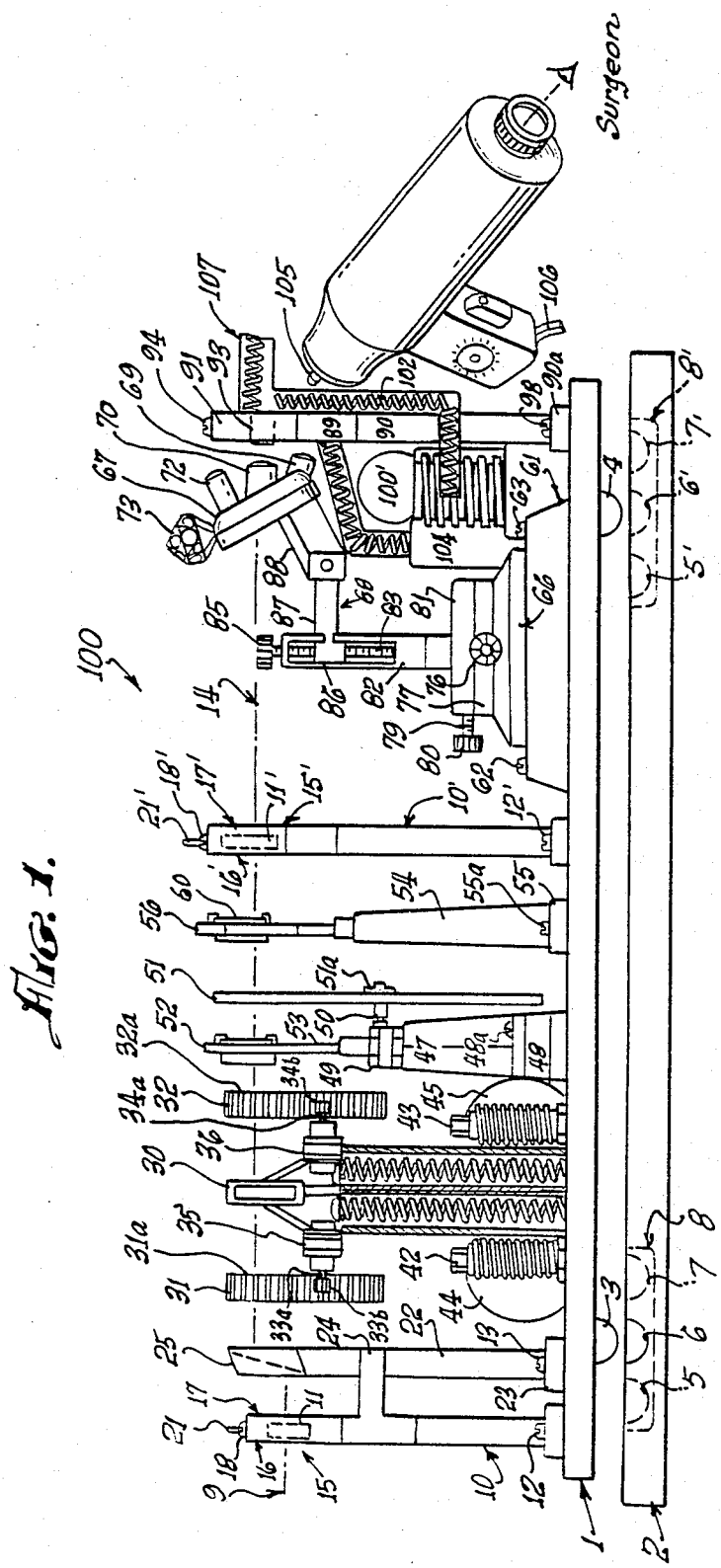
FIG. 1 is a side elevation of an improved coherent beam coupler in accordance with the invention.
Figure 2:
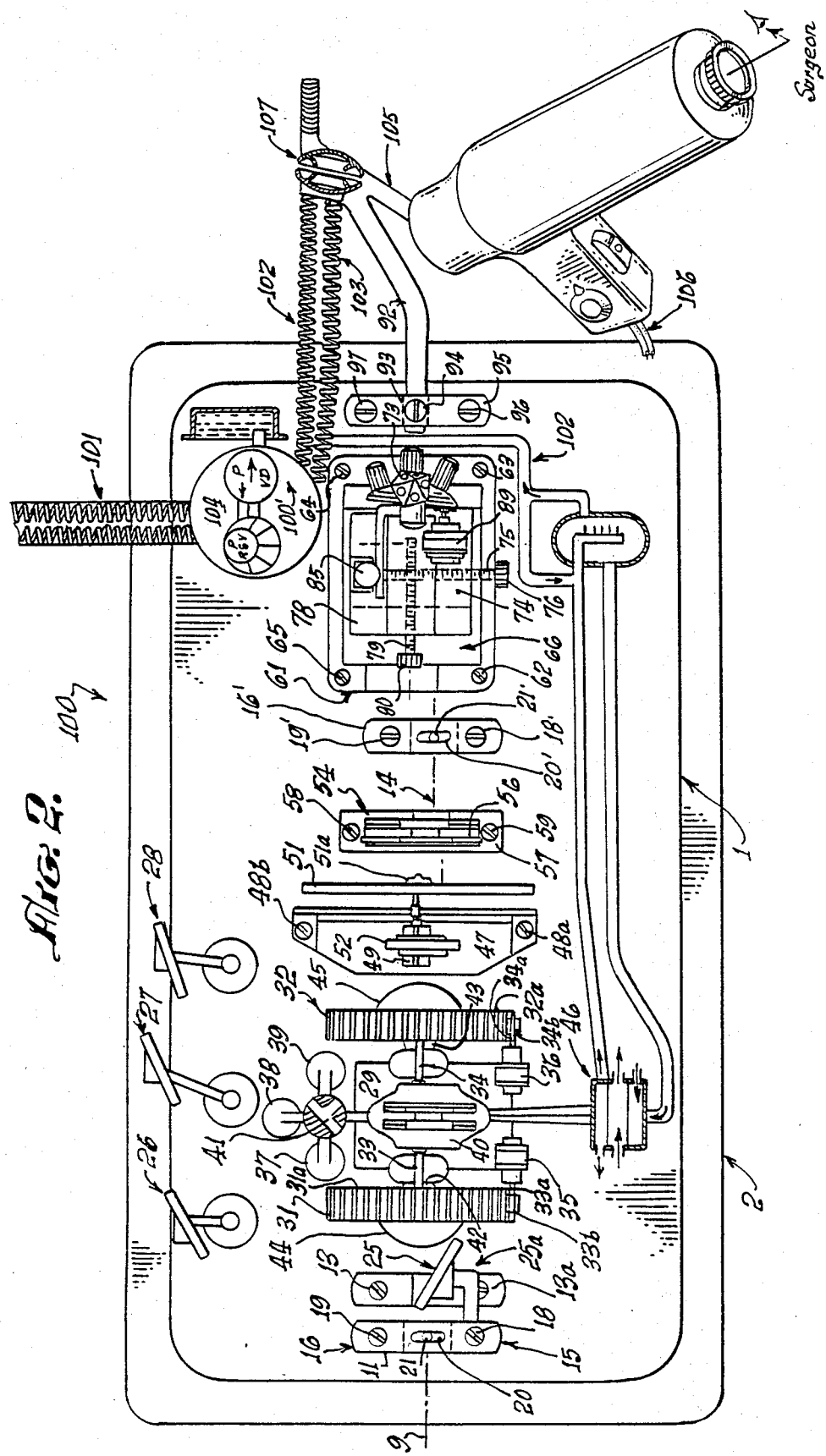
FIG. 2 is a plan view of the system depicted in FIG. 1.

Referring first to FIGS. 1 and 2, a coherent laser coupler 100 for directing laser light to selected sites includes a platform 1 composed of suitable commercially available materials, such as a composite material or the like. Beneath the platform 1 are disposed a plurality of magnetic attraction support elements in the form of ball bearings 3, 4. In the subject embodiment, two such magnetic attraction elements are depicted in the views provided. The magnetic attraction elements are in the subject embodiment symmetrically disposed beneath the platform 1.

The system further includes a lower stabilization plate 2 mountable upon a structure, such as a tripod or optics table (not shown). The bottom stabilization plate 2 defines a plurality of hemispherical recesses 6, 7, 8, and 6', 7', 8', the two series of hemispherical recesses corresponding to the location of magnetic elements 3, 4, respectively. Of course, similar hemispherical recesses are provided to accommodate the two magnetic elements not depicted in the views provided. Thus, a feature of adjustability relative to the position of the magnetic elements with respect to the respective recesses is provided.

Incoming laser radiation 9 is from a source not shown, which may be of any commercially available type, such as gas ion, solid state, or pulsar, or any other suitable source. Laser beam 9 is directed toward an adjustable iris diaphragm 11 within an upright support or bracket 10 which is fastened to platform 1 by screws 12, 13. As is more fully described hereinbelow, iris diaphragm 11 is of an electronic type, manually operable. In the depicted embodiment, diaphragm 11 has a minimum aperture of substantially 500 micrometers and a maximum aperture substantially equal to 20 millimeters. The optical axis of beam 9 is denoted by reference numeral 14.

Support 10 includes upper portions 15, 16, which contain cooling and structural elements described more fully hereinbelow. A securing bar 17 is secured to the support stand 10 by two screws 18, 19. Bar 17 defines a slot 20 for a manual override lever 21 utilized for adjusting diaphragm 11. A secondary diaphragm unit equivalent in design and structure may be disposed within the framework of the system. The numerical values assigned to each element of the secondary diaphragm unit are the same as the diaphragm unit 11 and are expressed by an equivalent number followed by a prime value indicated by numerals 10', 11' through 21', inclusive.

A support stand 22 having a base 23 is mounted on a support 24 and disposed adjacent support stand 10. The upper portion of support 24 contains beam splitter means 25. Beam splitter 25 is partly reflective and partially emissive, and is further aligned with the beam axis 14, and including a vertical rotating translator stage 25a, which is utilized to drive or rotate the beam splitter 25 along an axis, which is perpendicular to the optical beam axis 14 such that the splitter 25 can intercept the beam and various auxiliary beams not shown. Separate automated beam splitting means 26, 27, 28 afford the capability of dividing and directing one or more auxiliary beams towards unit 25 or directly down the optical beam axis 14.

A dye cell and pump complex 29 is disposed upon platform 1. Complex 29 includes element 30 comprising a quartz cuvette container which houses circulating dye (not shown) subject to being lased as it intercepts beam axis 14. Rotating wheels 31, 32, each of which contain a series of twelve separate partially reflective, partially emissive mirrors 31a, 32a of conventional type, are each mounted on revolving shafts, 33, 34, respectively. Shafts 33a, 34a are connected to their separate programmable D.C. motor units 35, 36 and rotate wheels 31, 32 by rotating gear means 33b, 34b. Dye reservoirs 37, 38, 39 are pressurized and feed into a pump member 40 via an automated triple valve release unit 41.

A solenoid inlet 42 and a solenoid outlet 43 are operatively associated with means 40. A mixing chamber 44 for dyes, and a reservoir 45 containing a suitable purging agent, are attached to the pump 40 and the dye cell 30. A combined heat sink and heat exchanger 46 for the entire complex 29 is disposed upon platform 1.

A support stand 47 having a base 48 is mounted on platform 1, secured by screws 48a, 48b, and is situated adjacent the dye pump complex 29. The support 47 contains a programmable D.C. motor 49. Motor 49 has a shaft 50 having rotor means 51 including spokes forming a chopper of conventional type having peripheral squared angular cut-outs. Rotor 51 is secured to shaft 50 by flywheel nut 51a and is positioned such that it can intercept beam axis 14 for the purpose of pulsing beam 9 and/or any auxiliary incident beams. The frequency and duration of the pulses can be adjusted by varying the speed at which the chopper rotates. In a particular application, the motor shaft is rotatable in a range of 1 rpm to in excess of 100,000 rpm.

An additional electric audioacoustical chopper 52 is affixed to support 47 by a bracket 53. Audioacoustic element 52 is disposed with its central axis aligned with the beam axis 14 so as to intercept beam 9 and/or any auxiliary incident beams and operates at a rate capable of modulating an emissive beam in excess of 50,000 interruptions per second.

A support stand 54 having a base 55 is mounted on platform 1 by screws, one of which is shown as 55a, is adjacent to support 47, which is located at the upper portion of stand 54, in which is housed an electronic shutter mechanism 56 alignable with beam axis 14. A horizontal bracket 57 secures unit 56 into position via two locking screws 58, 59. Shutter mechanism 60 is of commercially available type, including a timer and having a capacity to be manually operated by a plunger means (not shown) which is received in threaded orifice 227 (FIG. 5a).

A base element 61 is supported and secured to platform 1 by four thread screws 62, 63, 64, 65. An XYZ translational stage 66 is affixed to base element 61 and supports a motorized automated revolving turret structure supported upon support stand 68. The turret structure houses four micro objective lenses 69, 70, 71, 72 and a piezoelectric focusing and directional unit element 73. A slider 74 moves laterally in a pair of guide rails which can be adjusted by a threaded stem 75 including adjusting knob 76. Guide rails 74' for slider 74 are carried upon a slide 77 slideable longitudinally along another pair of rails (not shown) mounted on base member 61. Slider 78 is adjustable by a stem 79 with a knob 80. On slider 81 is an upright column 82 having a bore with openings in the side wall 83. A threaded stem 84 extends vertically in column 82 and has an adjusting knob 85 on its end. Carried on stem 84 is a threaded member 86 having an extending arm 87 which carries a turret mount holder 88. Holder 88 also houses a rotating automated motor 89 which rotates turret 67.

Thus, by adjustment of knobs 76, 80, 85, turret mount structure 88 is movable in any of three different planes to align a focusing lens or piezoelectric element with the beam axis 14.

An upright support and stabilization column 90 includes a base 90a mounted on platform 1. A housing 91 contains a fiber optics bundle 92 and is situated in a cavity 93. Housing 91 is secured by a set screw 94 incorporated into a horizontal clamp means 95 which is fastened to column 90 via threaded screws 96 and 97, as seen in FIG. 2. Column 90 is secured to the platform via screw 98 and another screw (not shown).

A bivalvular pump means 100' supplies a plasma infusion medium provided by a conduit 101 leading from a reservoir (not shown). A conduit 102 affords a means whereby the infusate can exit pump means 100'. The expended infusate returns via an outflow conduit 103, a filter unit and reservoir 104, which is incorporated in the pump proper 100' where it is prepared for recycling. The system further includes a directional fiber optics imager 105. Element 106 is a video link leading to a CRT imager, charged coupled device or similar such device. Both the video system 106 and fiber optics imager 105 are of commercially available type. An outgoing fiber optics cable 107 is utilized to transmit an emissive source and is of a type commercially available in bundles with elements ranging from one millimeter in diameter to less than 0.500 micrometer.

FIG. 3 depicts a more detailed view of the exterior diaphragm means. The upright support stand 10, the iris diaphragm 11, and screws 12, 13, passing through their respective foot mounts denoted by numeral 108, secure the entire structure to base platform 1. The upper portions of the stand 10 include heat sink and heat exchanger elements 109, 110, respectively. Slotted members, such as channel 20 accommodating the sliding motion of lever 21, and a circular containment channel 111 situated in members 10 and 17, are utilized to hold the diaphragm element 11 in a selected position, as seen in FIG. 3a.

As best shown in FIGS. 3b, 3d, twelve terminal fiber optics 112 through 123 are each of selected size, shape, and spatial location. Fiber optic elements form in part optical read-out bundle 124. The fiber optic elements 112 through 123 are held in their own separate containment areas 125 through 136, respectively. Diaphragm blades 137a through 137g are rotatably mounted on a common slide 137h, as seen in FIG. 3d, upon rotation of the diaphragm blades 137a through 137g along slide 137h, optics elements 112 through 123 are exposed one at a time to a long life (LED) diode 138 disposed on a rotating circular slide element 139, movable along its circular track 140, as the aperture 141 increases or decreases in size. Additional mechanical stop units 142, 143 prevent the aperture 141 from exceeding its maximum or minimum size, and thus prevent damage to the blade elements of the diaphragm.

Each unit 142, 143 has an outer mounting case 142a, 143a secured to the outer casing by threaded means 142b and 143b. Tension springs 142c and 143c provide the necessary torque to plunger elements 142d and 143d, preventing a variable reversible D.C. motor 144 from moving the aperture beyond its upper or lower limits. Motor 144 is depicted partially schematically in FIG. 3c as is a rotating shaft 145 and a rotating gear element 146 turns in such a manner as to engage a larger gear track element 147, circumferentially located in the diaphragm element proper, and rotating the diaphragm blade elements in their common track. Gear 147 is exposed to gear 146 through a slotted portion 148 of an outer casing 149 of diaphragm unit 11, as shown in FIG. 3d.

FIG. 3e constitutes a detailed view of heat exchanger elements, heat exchanger grids 109 and 110. The grid elements are each composed of a plurality of microcoiled helical heat exchanger tubules designated individually and collectively by numeral 151. Each microcoil tubule 151 is comprised of a suitable copper alloy and fluid well known to those skilled in the art. The upper portion is constructed of a suitable heat conducting material which conveys thermal energy from the diaphragm proper to elements 109, 110, where the excess heat is dissipated. The outer surface of each diaphragm is coated or electroplated with a layer 150 of a highly reflective chromium alloy; the outer case is coated or anodized with a non-reflective blacking compound, as are similar structures, such as the chopper and shutter means.

FIG. 3f is a highly simplified version of an optical encoding and optical interrupt sequencer. Diode sources comprise elements 152, 153 which are supplied with a common resistance (not shown). An LED source 154 is connected to miniature motor unit 155. A standard available microprocessor 156 is connected to common feedback elements 157. Comparators 158, 159 are connected to a keying module sequencer 160 comprising a series of known resistor elements.

Figure 3G:
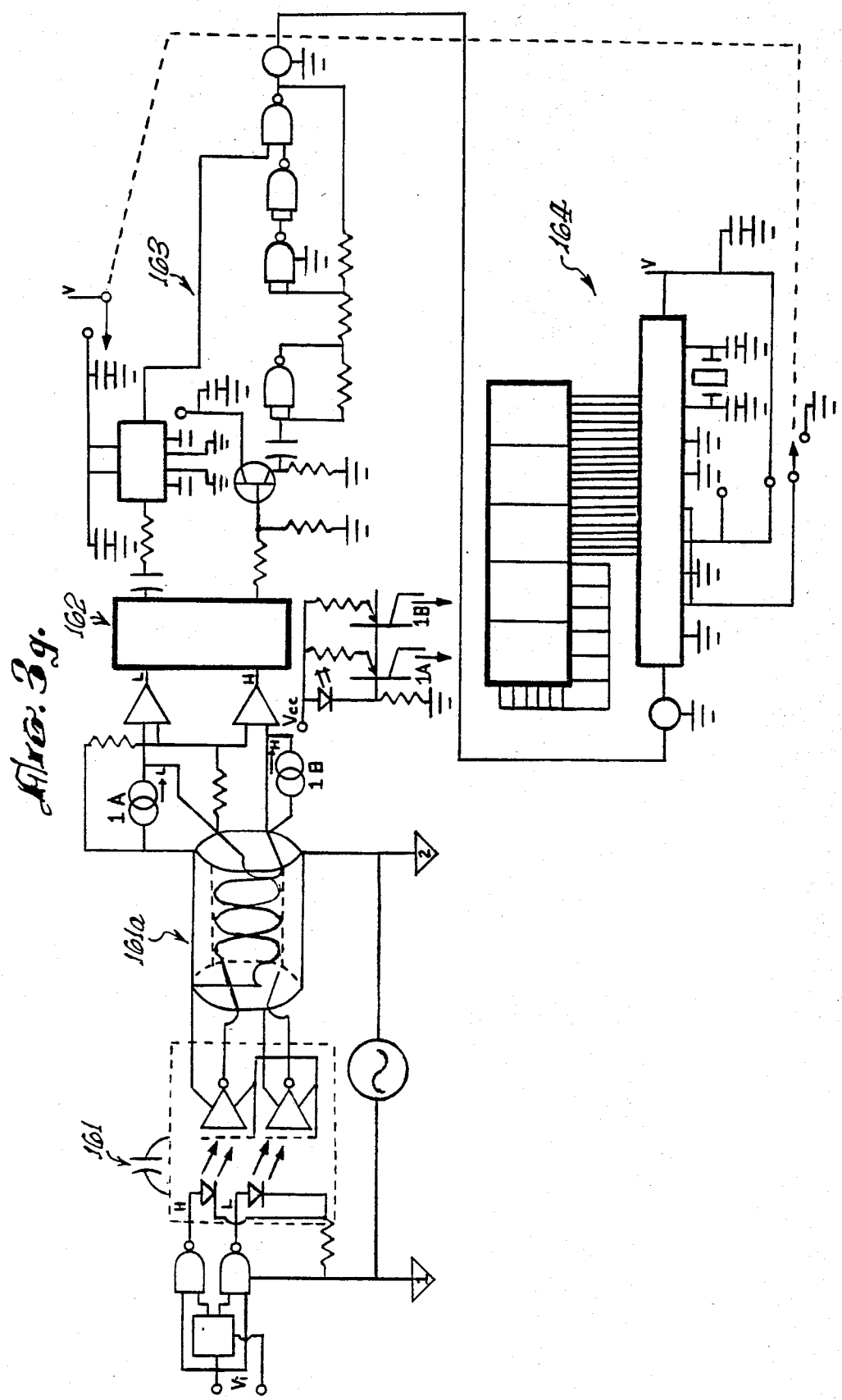
FIG. 3g is a detailed schematic representation of a fiber optic on-line system, signal digitizer, and numeric position display unit of the system of FIG. 1.

As depicted in FIG. 3g, a fiber optics on line coupling system signal digitizer and position display 161 numerically indicates aperture size. An optical line driver of conventional type is aligned with an optical transducer 161a, also of conventional type. The signals are digitized and multiplexed in flip-flop data element 162 and are compared to known gains as the signals are processed in auxiliary unit 163. The signals are received by a counter display unit 164 where the numerical values of position and aperture size are displayed. Reference numerals are assigned to entire subsystems of commercially available components rather than each individual component part.

FIG. 4 illustrates a cross-sectional view of one of four equivalent beam splitter units 165. Unit 165 includes a prismatic dielectric mirror element 166 and a pair of thermal conveying plates 167, 168. Mirror 166 is coated with suitable dielectric compound well known to those skilled in the art, capable of altering optical opacity to a slight degree and being selectively emissive. The wavelength characteristics of mirror 166 are selectively adjustable based on the coating and dielectric charge in contrast to conventional beam splitters having fixed characteristics. The thermal plates 167, 168 are composed of suitable thermal material and have the capability of transmitting heat from element 166 along its circumferential rim to two layered plates 169, 170, comprising heat dissipation means formed of microcoiled miniature helical tubules functioning as heat exchangers. Each helical tubule 171 transverses the length and breadth of plate elements 167, 168; and elements 175 through 180 comprising a plurality of microplates and helical microtubules forming heat exchange elements, as shown in FIG. 4a.

Dielectric mirror 166 is chargeable to increase optical opacity by a capacitance unit 172 and undergoes decreases in optical opacity when discharged by capacitance unit 173. A vertical angular socket joint 174 is provided to rotate the entire plate housing holder 165 vertically through 180 degrees of arc. A rotating shaft element 181 rotates the unit 165 horizontally through 360 degrees of arc and is secured to a sleeve 182 in which it is inserted through an outer casing 183.

Outer casing 183 includes a threaded rotational channel 184 in which a threaded member 185 turns shaft 181. Bolts 186, 187 fasten the outer casing halves 188, 189 and a common gasket 190 together. A chamber 191 is filled with a suitable low friction lubricant to decrease wear on a rotating ball bearing system 192. Ball bearing system 192 is attached to the internal mainframe by a series of stationary sleeves 193 acting for stabilizing the rotating shaft 181. A miniature synchronous D.C. motor 194 is reversible and programmed through a moderator 195. The software and sensor systems (not shown) for the beam splitter means are preferably of a commercially available type well-known by those skilled in the art.

FIG. 5 depicts in detail a housing for the shutter mechanism. The housing 221 is mounted on a base 196 attached to platform 1 and attached thereto by threaded screws 197, 198. The stand 54 includes a support member 199 having feet 200, 201 which are secured to a subplatform 202. A vertically movable shutter stage 203 has a V-shaped slot and rests on legs 204, 205. Legs 204, 205 are movable in bores 206, 207 and glide in plate 208 which is supported above member 209. A lead screw 210 extends through threaded bore 211 of a linear guide plate 212. Lead screw 210 is rotatable by a knurled knob 213 pivotably mounted in slot 215 in member 216. Knob 213 is carried by member 214 and is manually rotatable to adjust and reset the shutter means stage 217. A clockwise rotation translates the stage 217 upwards; counterclockwise rotation translates stage 217 downwards. The shutter means is positioned and held in retaining cavity 218. Cavity 218 is positioned between two linear heat conducting plates 219, 220 which are constructed of a suitable conventional material. A bracket 221 and slide secures members 218 through 220, together with ancillary heat dissipation units 222, 223. Bracket 221 is fastened to the mainframe of the stand by threaded screws 224, 225. Heat is conveyed by plates 219, 220 to heat exchangers 222, 223, respectively. The heat exchangers are depicted to be rectangular in shape and are equivalent to the plurality of helical microcoiled tubular heat exchangers referred to hereinabove.

FIG. 5b discloses in greater detail units 222, 223, comprising a single exemplary microcoiled heat exchanger unit by element 224'.

FIG. 5a illustrates an electronic shutter mechanism. The shutter includes an outer casing 225 of a shutter element 226. The shutter mechanism also includes a threaded acceptor means 227 for a manual reset and firing plunger (not shown). The plunger inserts into a spring-loaded recoil element 228 which engages a pivotal slide 229. A firing solenoid 230 for closing the shutter which is of a diaphragm type pushes a pivot 231 along a slide while solenoid 232 pushes pivot 233 to open the shutter, the opening solenoid being a novel modification over the spring-loaded return of the conventional shutter means. Two charging coils 234, 235 connected with their respective capacitor banks 236, 237 power the aforementioned solenoids. An optical electronic sensor relay and microprocessor complex 238 provides the main timing element. Units 239 through 242 are auxiliary modules providing for alternation in oscillation frequency and timing sequence for the shutter.

FIG. 5c is a schematic representation of a frequency oscillation circuit and timing sequencer of conventional type. Circuit 239 includes a main input channel and accessor 243, a main timing sequencer 244 containing a complement of comparator microprocessors, and a strobing output and reset channel 245 consisting of a plurality of microprocessors and auxiliary electronic components of conventional type. Reference numerals are assigned to entire subsystems rather than their separate component parts.

FIG. 6 depicts a more detailed view of infusion pump means 246. Pump 246 comprises two cycling units 247, 248 operated by a reversible variable motor 249. Motor 249 is of commercially available type including capacitor means 250 and regulator means 251. The motor 249 is fastened to platform 1 by two platform feet 252, 253 held in place by screws 254, 255, 256, 257. The foot members are formed from stabilizing rocker brackets 258, 259 welded to the outer casing 260 of the motor 249.

An online feedback and control mechanism 261 is connected to a feedback and control system of conventional type (not shown). An outer coupling 262 is connected to the motor 249 which rotates a shaft 263. An outer coupling 264 of the motor shaft 263 extends through a cam of separate pump means 264, 265 of the dual pump means 247. Shaft 263 passes through a hermetically sealed plate 266 and through both pump means, terminating at a hermetically sealed ball bearing and sprocket 267 at the opposite end of pump means 247.

A ball bearing system 267 is welded to a hermetically sealed plate 268 secured to pump mainframe 262 by four bolts (three of which are shown: 269, 270, 271). The pump mainframe 272 includes a threaded aperture 272a for the fourth bolt (not shown). A sealing gasket 272b is provided to prevent seepage of infusate from chamber 273, as a conical vane member 274 is rotated by shaft element 263, which is slotted and at coupling 264 is provided an optical electronic rotational monitor (not shown). Flow channels 275, 276, 277, 278 include electronic magnetic flow sensors 279, 280, 281, 282, which are employed to measure the flow rate and which are of conventional type. Each of the centrifugal pumps are isolated from one another and mounted to platform 1 by their own mounting bracket 283 formed from the pump mainframe 272. Bracket 283 is secured by four support feet 283a through 283d, three of which are depicted. Each foot accommodates two securing bolts (four of which are depicted). (Two bolts 283e and 283f of foot 283c are shown in the figure as are bolts 283g and 283h of foot means 283d). Conduit 284 provides infusate from a reservoir (not shown) to centrifugal pump 264; a valve 285 governs inflow of an aspiration medium into centrifugal pump 265 from another reservoir (also not shown). The pumps are equivalent to each other except that pump 265 has a higher torque output value, as required for purposes of aspiration. Flow rates into and out of each pump are equivalent to maintain the hydraulic integrity of vessels connected thereto.

FIG. 7 comprises a detailed partial sectional view of the upper portion of column 89. Emissive fiber optics bundle 92 includes self-focusing elements 288. Bundle 92 is positioned within a sleeve 287 contained within cavity 93 and held by a screw 94. An additional self-focusing fiber optics bundle 288 is contained in a sleeve 289. A sleeve 289a for a bifurcating conduit system 290 is attached to column 89.

Conduit system 290 carries plasma infusion and aspiration lines 291, 292 which are disposed along the outer periphery of the fiber optics bundles 92, 286. Each of the fiber optics bundles 92, 286 consist of at least ten separate elements but in most applications may contain more than one hundred separate elements of commercially available type. A flexible conduit 302 contains elements 92, 286, 291, and 292, conduit 302 comprising outer and inner coated stainless steel casings 302a, 302b.

Figure 8:
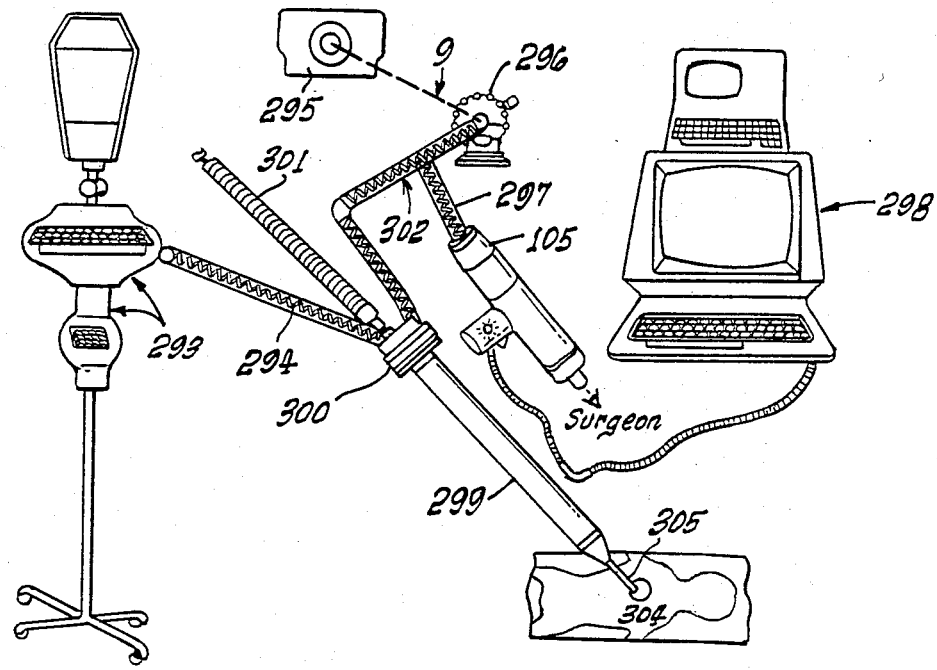
FIG. 8 is an illustrative representation of insertion of a catheter needle.

FIG. 8 discloses a partial and simplified depiction of some ancillary support systems for the invention. Automated reservoirs 293 operate for both the infusate and aspirate, each of which is conveyed to the pump system via conduit 294. A laser emissive element 295 operates via emission beam 9 which is incident upon a coupler device 296. An exit cable 297 is connected to self-focusing fiber optics means 105 which is patched into a high resolution video enhancement computer complex 298. A conventional hypodermic means element 299 is equipped with a hermetically sealed hydraulic member 300 which is supplied with hydraulic fluid by a miniature pressurized tubular valve line 301. Means 301 is supplied with an internal sleeve (not shown) which advances or withdraws conduit means 302. Conduit means 302 exiting from coupler 296 enters the hypodermic 299 and feeds directly into hydraulic member 300 via one of two circular gasket solenoid assemblies 303, 308. Units 303, 308 provide a leakproof seal for forward or backward mobility of conduit 302, which is shown in greater detail in FIG. 9a. The operative site 304 is depicted in schematic view of the body of the patient on whom the procedure is to be performed. A catheter needle 305, through which conduit 302 passes to reach the site 304, is of conventional type.

METHODS OF INSERTION AND INFUSION

Figure 9:
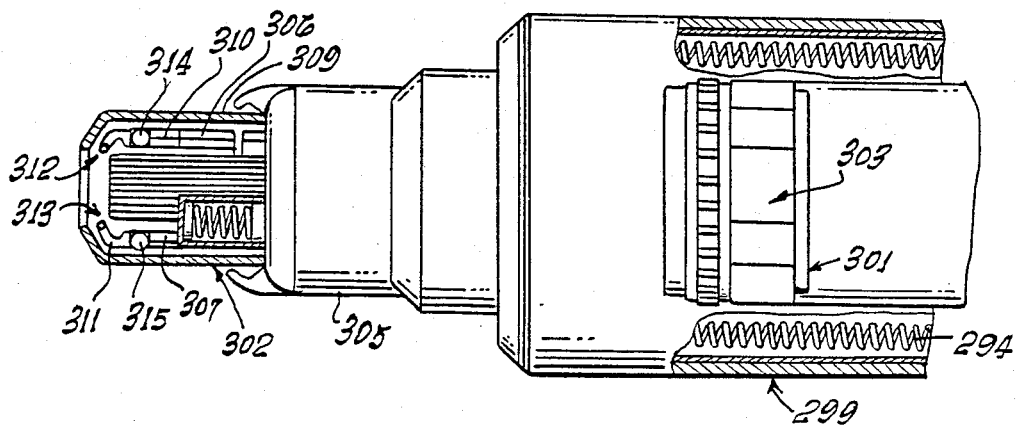
FIG. 9 is a detailed enlarged cross-sectional view of a portion of the system of FIG. 1, including a catheter needle and associated elements.
Figure 9B:
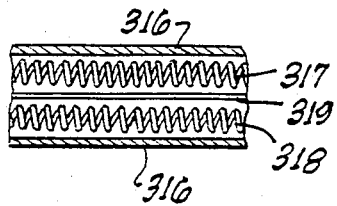
FIG. 9b is a detail view of one conduit structure in the assembly of FIG. 9.

FIG. 9 is an enlarged detailed cross-sectional view of main conduit 302, catheter needle 305, and a portion of syringe 299. The process of hypodermic insertion is well understood and conventional and will be thus described only briefly. Essentially, an element is injected into the body of an organism and positioned by mechanical means. In accordance with the invention, employment of a hydraulic means provides the capability for versatile and novel deployment of catheter element 302. Conduit 302 houses optics bundles 92, 286, together with separate conduit lines 306, 307. While the hydraulic means provides motion for element 302 by the two equivalent solenoid rings 303, 308, ring unit 303 prevents leakage of plasma from the syringe unit or the back flow of hemopoetic material from a vein or artery.

Figure 9A:
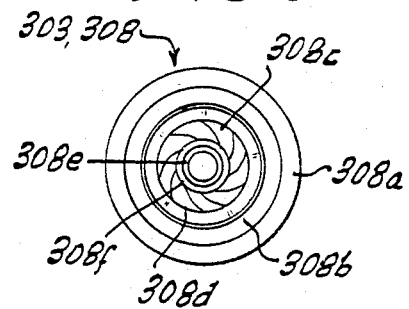
FIG. 9a is a detail view of one clamping means of the assembly of FIG. 9.

FIG. 9a depicts ring unit 308 which includes an outer casing 308a, an inner sleeve 308b, and a variable clamping diaphragm 308c rotating along a slide 308d and powered by two miniature solenoid elements (not shown) of conventional type. Two soft interlocking gaskets 308e, 308f made of a suitable material, such as polyethylene, provide an air-tight seal. The gaskets abut against conduit 302 and secure it in position until it is either advanced or withdrawn. The tension exerted by gaskets 308e, 308f is significantly less when element 302 is in motion and it is supple enough to provide an effective seal to prevent leakage.

The catheter needle 305 is of sufficient size or diameter to allow element 302 to pass through with a clearance of at least 10 percent and to allow a small curtain of isotonic plasma to be released from the syringe 299 in order to provide a lubricant for conduit 302. A flexible heparenated stainless steel outer casing 309 and bundles 92 and 288 are disposed between identical conduits 310, 311. Conduit 310 conducts a stream of isotonic saline and heparen, and conduit 311 provides a means to supply an aspirant and aspires the stream of 310 back toward the aforesaid filter and reservoir. A nozzle 312 of structure 310 directs flows of infusate and similar media, while a nozzle 313 directs flows of an aspirant and provides aspiration for the infusate and all materials in the vicinity of elements 92, 286. A jet stream of infusate and heparen medium displaces hemopoetic constituents when conduit 302 is within several millimeters of the target site 304. The displacement process involving the continuous flow of infusate provides an optically clear and emissive curtain in which to sight the target and through which to fire emissive beams. The displacement process is discussed in greater detail hereinbelow.

The optically emissive curtain prevents hemopoetic materials, such as erythrocytes, platelets, and other blood constituents or residues from adhering to the surfaces of the emissive fiber and to subsequently fusing to particular fibers resulting from the substantial heat generated by the emissive beam. The curtain is continuously withdrawn by aspiration and simultaneously replaced, providing a constantly renewable source. Each tubular unit is associated with a feedback member, such as miniature magnetic flow meters 314, 315, which monitor pressure. The feedback mechanism is of conventional type. It provides a means whereby the internal ambient pressure of a vessel is maintained substantially constant, thus preventing blowouts of the vessel so that once the flow is in equilibrium, the net output flow of one nozzle conduit 312 exactly equals the net input flow of the other nozzle conduit 313.

FIG. 9a is a more detailed cross-sectional, partial view of a portion of conduit 310 (the same as conduit 311). Conduit 310 includes a flexible outer casing 316. Coiled conduit 317 conveys the plasma infusate, and coiled conduit 318 conveys the heparen medium to prevent clotting. Conduit 310 further includes a flexible stainless steel separator in the form of a nylon cable 319. The entire process of insertion and the actual infusion takes approximately two minutes. The infusion process itself is sequential, consuming one to ten seconds, and corresponding to intervals of lasing or imaging of the target site.

METHOD UTILIZING THE DEPARTICLIZATION PROCESS

The departiclization procedure is a novel process whereby chemical constituents undergo a lasing sequence in the presence of a renewable moderator. The physical structure and chemical nature of treated or processed substances at or near an aberrant or diseased site are modified on a molecular level, as described more fully hereinbelow. In accordance with the invention, the electronic characteristics of an emissive source are modified, based on information or data, returning from emissive wavelengths. First, the target site, whether a papular body, carcinogenic tumor, or clotted artery, or similar lesion is sighted. A low-level laser emission is directed onto the target site in order to thermally excite a local portion of the site. The returning laser beam in the form of a thermal emission is reflected back and/or reemitted with a shift in its wavelength. The doppler velocity and altered wave characteristics are compared to the net incident beam, so that by the difference, the density, size, and chemical composition of the target site can be computed. The doppler determination is a new application of a recognized technique, known to those skilled in the art.

After the density, size, and chemical nature of the target site are computed, the coupler 296 is automated to lock onto and deliver an emissive beam toward the given target site. Such emissive beam delivered by the coupler 296 will be of a predetermined exposure sequence and electronic composition so as not to disintegrate or adversely affect healthy regions adjacent the aberrant site, as for example by overshooting and puncturing an arterial wall. Papular bodies lying in vessels or other structures, such as heart valves, or diseased sites in the pancreas, or other inaccessible locations are similarly treated. Thermal conditions of the moderator are also monitored and controlled, in order to prevent hydraulic blowout of a given vessel, or the relocation of an occlusion, due to thermal vasodilation of the affected vessel, to one or more remote or inaccessible sites.

The departicalization process, when examined under high resolution, in thermographic studies in vitro and vivo, indicates that insoluble or chemically active constituents composing a given aberrant structure undergo molecular reconstitution, to a soluble, relatively non-reactive, voidable substance.

As noted above, under departiclization molecules are subjected to intense localized thermal agitation or bombardment in the presence of a suitable inert, optically emissive moderator. The moderator in the case of the biological system referred to hereinabove was composed almost exclusively of plasma saline infusate. High resolution video thermographic studies indicate that in some instances substances, such as cholesterol, insoluble fatty acids, and carcinogenic or benign papular bodies composed of proteinoids, react in a manner to implode thermally upon disintegration, in the presence of the local moderator. They then undergo rapid cooling, and chemically recombine with one another to form similar globular structures ranging from 10 to 40 microns in diameter. The smaller globular or irregular spheroid structures resulting from the departiculization process are, as in the case of declotting vessels, rendered blood soluble, and can undergo rapid absorption elimination by such natural bodily processes as phagocytosis. The disclosed process of departiculization is one of rapid successive, local microsectioning, and cauterization, hereto unachievable by other laser processes.

FIG. 10 depicts in simplified form some of the instrumentation utilized in the doppler analysis process. The instrumentation comprises a new combination of existing elements included in the coupler 296.

FIG. 10 depicts in a block diagram fashion only one of several measuring apparatus or cuvette pairs, which provide continuous analysis of a given target site, at any given time. Several hundreds or thousands of sites can be simultaneously scanned and analyzed by the same instrumentation, if more cuvette pairs are utilized. A single pair of cuvettes 400, 401 continuously measures the changes in the optical wavelength, and charges of the circulating effluents. Cuvette 401 serves as a reference and contains a standard of known concentration; the other cuvette 400 is continuously filled with the vaporized effluent which is aspirated back from the target site. The samples may or may not be subjected to microelectrophoresis. A constant flow pump regulator 402 provides a constant flow rate. A refrigeration unit 403 maintains the effluent at a substantially constant temperature. An oscilloscope potentiometric and analog recorder complex 404 records the charges and wave difference of the effluent. An auxiliary automated monochronometer 405 scans known wavelengths. Also included in the system is an auxiliary photomultiplier tube and microspectrometric complex 406. A plurality of emissive laser sources 407, 407a, 407b, 407c provide either continuous, sequential, separate, or simultaneous emissions to the coupler 100. The laser wavelengths as indicated by the laser types generate emissive wavelengths ranging from ultraviolet to the extreme infrared region of the spectrum. Further included in the system are an analog squarer multichannel analyzer 408, 408a and central recording data processing unit 409. The squarer 408 provides analog information, and the multichannel analyzer 408a serves as a digital comparator with a memory of all known wavelengths of all known substances in various concentrations. Once the values are compared and the proper elements identified, the data matrix is fed into a central computer complex 410 in which all optical and electronic signals are differenced in such a manner as to determine the ultimate duration, intensity, and optimum electronic characteristics for the incident beam needed to obliterate a given aberration without damaging any region in the vicinity of the target site.

Data conduits 411, 412 supply emissive input and return output to and from an affected target site, a series of conduits 413 circulate coolant and a series of elements 414 provide a capability of bidirectional optical action. Auxiliary optical electronic cables 415 supply coupler means 100. Cables 416 provide additional coaxial input/output relative to elements 408, 409, 410.

Three boundary layers are associated with the target site. They are: a surrounding area, which incorporates the intima; the aqueous fluid medium, which surrounds the target site; and/or other underlying structures in proximity to the target area. The departicalization process is advantageously treated as a series of discrete steps. Spectral signals representing spatial and temporal data are digitized and taken in discrete intervals. The intervals are arranged in various information matrices for enhanced images.

An estimate of the temperature of the target tissue as a function of time is necessary to give the observer data concerning the optimum pulse length. If the laser pulse is longer than the optimum pulse length, heat will be exhausted through dissipation to the surrounding region. When tissues are regarded as capacitance systems having a capacity to store energy for a finite period of time, and then radiating the same stored energy as heat, tissue damage can be avoided by controlling delivery of a given amount of energy for a predetermined time interval. Two cases involving heating are considered. In the first case, energy from a laser is considered to produce a rise in temperature in a cylindrical volume in the target and surrounding tissues, and that heat flows radially outward therefrom. In the second case, it is considered that there is an absorption upsurge in only a relatively shallow surface layer of the tissue being irradiated. The actual time necessary for the optimum pulse length falls between the estimates based upon the first and second cases.

Case 1: Absorption in a Cylindrical Volume

This case is predicated upon a radially gaussian distribution of laser energy given by $$I_{Laser} = I_0 \rho - \frac{r^2}{2r_0^2}.$$

Where r is an approximation of the radius of the laser spot, the heat diffusion equation in cylindrical coordinates is:

$$\nabla^2 T = \frac{\rho c}{K} \frac{\partial T}{\partial t}$$

Where
C = specific heat
K = heat conductivity
$\rho$ = density
T = (z,r,e,t).

If we assume $$\frac{\partial T}{\partial t} = \frac{\partial T}{\partial \theta} = 0, \text{ then } \frac{\rho c}{k} \frac{\partial T}{\partial t} = \frac{1}{r} \frac{\partial}{\partial r}\left(r \frac{\partial T}{\partial r}(r,t)\right),$$

and we may let $T(r,t) = -U^2 T(r)T(t)$.

The radial part is Bessel's i.e. with solutions:

$$T(r,o) = A(u) J_0(ru)\rho - \frac{u^2 k}{\rho c}$$

We require $$\text{at } t = o, T(r,t = u) = T_0\rho - \frac{r^2}{2r_0^2}$$

A (U) is selected to make the solution match the i.e. using a Fourier-Bessel transform.
From Watson we get $$T(r,t) = r_0^2 \int_0^\infty r J_0(\nu,r) \rho - \left(\frac{kt}{\rho c} + \frac{r_0^2}{2}\right) r^2 d\nu$$

To estimate the time necessary for the dissipation of a heating effect we set:

$$\frac{T(r,t)}{T(r,o)} = \frac{1}{2} \text{ at } r = c \text{ this reduces to } \frac{2Kt}{r^\rho \rho c} = 1 \text{ or } t = \frac{1}{2} \frac{r_0^2 \rho c}{k}$$

In the second case it is assumed that complete energy absorption will initially take place at the surface and neglect the radial dependence of the laser energy:

$$\frac{\partial T}{\partial r} = \frac{\partial T}{\partial \theta} = 0$$

The heat diffusion equation becomes upon separation of variables:

$$\frac{1}{T(Z)} \frac{\partial^2 T(z)}{\partial Z^2} = -\nu^2 = \frac{1}{T(t)} \frac{\partial T}{\partial t} \frac{\rho c}{k}$$

This has solutions of the form:

$$T(z,t) = A(\nu) \cos(\nu,z)\rho - \frac{rkt}{\rho c}$$

For initial conditions we choose: $T(o,z) = T_o U(Z_o - z)$. Where $$U(z_o - z) = 1, o < z < Z_o$$
$$= 0, z \geq Z_o$$

This means that energy is deposited in a layer of thickness Zo, i.e., that T(Zo) = (constant)X(energy in laser pulse). A solution may be obtained by assuming $T(Z,t=o) \cong \delta(z)$.

We again require A(v) to match the i.e.:

$$T(o,z) = \int_0^\infty A(\nu) \cos(\nu,z) d\nu \text{ so that } A(\nu) =$$

$$\frac{2}{\pi} \int_0^\infty T(u,z) \cos(u,z) dz \, T(z,t) =$$

$$\int_0^\infty A(u) \cos(u,z) \rho - \frac{uztk}{\rho c} du =$$

$$\frac{T_o}{2} \sqrt{\frac{\rho c}{nkt}} \int_0^{z_0} \left\{ \rho - (x+z)\frac{z\rho c}{4kt} 1 - \rho - (x-z)^2 \frac{\rho c}{4kt} \right\}$$

The solution at z = o reduces to:

$$T(o,t) = \frac{zT_o}{\sqrt{r}} \int_0^{z0} \frac{\sqrt{\rho c}}{4kt} \rho - \nu^2 d\nu = T\rho rf\left(z_o \frac{\sqrt{\rho c}}{4kt}\right)$$

From tables, the time required fo the temperature to drop to 52% of its initial value gives us the condition:

$$\frac{1}{2} = Z_o \sqrt{\frac{\rho c}{4kt}} \text{ or } t = \frac{Z_o^2 \rho c}{k}$$

estimated surface absorption dt for 52% init. The fluid dynamics of the departicalization procedure and the effects of indirect joule heating on boundary zones, such as vessel walls, infusate, and associated structures, are as follows.

The fluid temperature is regarded as having a uniform ambient temperature until a sudden alteration in thermal continuity occurs due to joule heating. The laser emission source provides joule heating and a maximum flow rate which can be achieved in a relatively short distance from the emission's source. The maximum flow rate which can be exacted from an initial static condition, which results from an occlusion obstructing the flow rate from 25% to 99+%, is a velocity which is essentially parabolic (laminar flow).

A sudden discontinuity, such as a blood clot, can be depicted mathematically as follows:

$$\text{Velocity } U(\eta) = \bar{U}\max\left(1 - \frac{\gamma^1}{\gamma o^1}\right)$$

where U max is the centerline velocity i.e. $\gamma = o, U = U$ max, $\gamma o =$ radius of the tube.

The governing equation utilized to describe the surrounding fluid medium adjacent to and surrounding the clot is:

$$U\frac{\partial T}{\partial x} = \frac{\alpha}{\gamma} \frac{\partial}{\partial r}\left(\gamma \frac{\partial T}{\partial \gamma}\right), \gamma = \frac{K}{\partial cp}.$$

Here, the fluid in contact with the clot is an aqueous preparation of buffered isotonic saline in distilled water.
K = conductivity
$\rho$ = density
Cp = heat capacity.
The boundary conditions are:
at $x \leq o$, $T = To$
at $x > o$, $T(\gamma o, x) = Tw$
The solution is $$T^*(\gamma^*, x) = \sum_{\eta To}^{\alpha} Cn fn(\gamma^*)\rho - \lambda^2 nx^*$$

$$T^* = \frac{Tw - T}{Tw - To}, \gamma^* = \frac{\gamma}{\gamma o}, x^* = \frac{x}{(2\gamma o)RePr\gamma}$$

where $$Re = \frac{U\max \gamma o}{\left(\frac{\mu}{\rho}\right)} = \text{Reyn. Number and } Pr = \frac{Cp\mu}{K} = \text{Prandh Number}$$

The secondary joule heating effects due to thermal exchange between the fluid medium and a given arterial or veinous wall can be expressed. The functions of fn are characteristic solutions to $$\rightarrow \gamma^* \frac{\partial^2 fn}{\partial \gamma^{*2}} + \frac{\partial fn}{\partial \gamma^*} + \lambda_n^2 \gamma^*(1 - \gamma^{*2})fn = o.$$

$fn(o) = 1$ for simplicity, and force $fn(1) = o$ to satisfy the wall temperature condition $T^*(1, X^*) = o$:

$$Cn = \frac{\int_0^{o\gamma^*(1 - \gamma^{*2})fn d\gamma^*}}{\int_0^{\gamma^*(1 - \gamma^{*2})fn d\gamma^*}}$$

The boundary conditions $fn(1) = o$ and $fn(o) = 1$ are satisfied only for certain discrete values of $\lambda n$. The eigen values are the graetz functions fn. (The values of various constants of $\lambda n$ are given in standard tables).

An explicit equation for developing tube velocity is given by the following:

$$\frac{U}{U\max} = (1 - \gamma^{*2}) - \sum_{\eta z 1}^{\alpha} \frac{8Jo(\lambda n \gamma^*)}{\lambda^3 n J_1(\lambda n)} \exp\left(-\lambda^2 n \frac{\gamma t}{\gamma o^2}\right)$$

Temperature profiles at various Prandh numbers for developing tube velocity may be obtained in standard works, such as F. M. White, "Viscous Fluid Flow." Here it is assumed that when an occlusion is completely eliminated, the flow rate will return to normal as long as the walls of the vessel maintain their integrity.

A normalized innovation process employed in accordance with the invention is set forth hereinbelow.

Discrete System:
$x(k+1) = \Phi x(k) + GU(k) + \gamma w(k)$ $z(k) = Hx(k) + V(k), K = o, 1, \ldots$ $E(W(t)W^T(T)) = Q\delta(t-r), E(v(t)V^T(T)) = R\delta(t-r)$ Normalized Innovation Process $V = (HPH^T + R)^{-\frac{1}{2}} (z - Hx) x (k + 1) = \Phi x(k) + Gu(k) +$ $k(k) vk [V(k + 1)V^T(k)] = (HP(k + 1)H^T +$ $R)^{-\frac{1}{2}} (z(k + 1) - Hx(k + 1))(z(k) - Hx(k))^T (HP(k)H^T + R)^{-\frac{1}{2}}$ $Z(k + 1) = Hx(k + 1) + V(k + 1) = H(\Phi x(k) + Gu(k) +$ $\gamma w(k)) + V(k + 1) Z(k + 1) - Hx(k + 1) = H\Phi \tilde{x}(k) +$ $H\gamma W(k) + V(k + 1) - Hk(k)[HP(k)H + R]^{-\frac{1}{2}} [z(k)] -$
$Hx(k)] = H\Phi \tilde{x}(k) + H\gamma W(k) + V(k + 1) - Hk(k) \Sigma^{-\frac{1}{2}}[H\tilde{x}(k) +$ $v(k)] = (H\Phi - Hk(k)\Sigma^{-\frac{1}{2}}(k)H)\tilde{x}(k) + H\gamma W(k) +$ $V(k + 1) - Hk(k)\Sigma^{-\frac{1}{2}}(k)v(k)E\{[z(k + 1) - Hx(k + 1)][z(k) - Hx(k)]^T\},$ $\Sigma(k) = HPH + R E\{[(H\Phi - Hk(k)\Sigma^{-\frac{1}{2}}(k)H)\tilde{x}(k) + H\gamma W(k) +$ $V(k + 1) - Hk(k)\Sigma^{-\frac{1}{2}}(k)v(k)][H\tilde{x}(k) + v(k)]^T\} =$ $[H\Phi - Hk(k)\Sigma^{-\frac{1}{2}}(k)H]P(k)H^T Hk(k)\Sigma^{-\frac{1}{2}}(k)R(k) =$ $H\Phi P(k)H^T - Hk(k)\Sigma^{-\frac{1}{2}}(k)(HPH + R(k)) = H\Phi PH^T - Hk\Sigma^{-\frac{1}{2}}\Sigma =$ $H[\Phi P(k)H - K(k)^{\frac{1}{2}}\Sigma] \cdot k(k) = \Phi PH\Sigma^{-\frac{1}{2}}$ in order to have the expected value of zero.

A more elementary expression is needed to describe the radiant exposure of an emission source which impacts on each unit area of a target site. Let RE represent the energy impacting per unit area of a target site, H targ., such that RE = $\int_o^T H$ targ. dt, which will give a value in joules/cm. The value H targ. = $\partial U/\partial t$, which has a value in watts per joule-second. U in the expression is equivalent to $U = \int_o^T N dt$ which gives a value in joules. (N is the number of watts delivered in a cylindrical volume per a given time interval.)

The case of deploying an energy source for the purpose of illuminating a given area, as preformed in diagnosis, differs drastically from the process of departicalization or resectioning. The energy utilized to illuminate an area is described as the luminous energy. The term for luminous energy can be represented in the expression $L = \int_o^T F dt$, which gives a value in lumen/sec or talbots. F in the expression is the luminous energy per unit time and is in fact measured in lumens such that $F = \partial L/\partial t$.

The simplified expression $E = \partial F/\partial A$ may be utilized to depict the luminous power reflected or transilluminated by a target site to a sensor array $$\left( \frac{\partial F}{\partial A} = \frac{\text{lumen}}{\text{meter}^2} \right).$$

The intensity of power per unit solid angle per unit source can be expressed in terms of $$\left( \frac{\partial F}{\partial A} = \frac{\text{lumen}}{\text{meter}^2} \right).$$

The light images can be enhanced, electronically processed, and arranged in the form of an information matrix format.

Optical spectra signals and spatial temporal data information can be arranged, when digitized, into an information matrix in connection with analysis of laser light.

$$J = \delta\left[ \left( \frac{\partial \ln L}{\partial b} \right) \left( \frac{\partial \ln L}{\partial b} \right)^1 \right] = \delta\left[ \frac{\partial^2 \ln L}{\partial b \partial b^1} \right]$$

J is designated the information matrix (Fisher)

$$Y = Ub + n$$

$$p(n) = \frac{1}{(2\pi)^{k/2} |N|^{\frac{1}{2}}} \exp[-\tfrac{1}{2} n' N^{-1} n]$$

An application of the Cramer-Rao inequality yielding the likelihood function.

$$L\{y;b\} = \frac{1}{(2\pi)^{k/2} |N|^{\frac{1}{2}}} \exp[-\tfrac{1}{2}(y - Ub)' N^{-1}(y - Ub)]$$

$$pnL\{y;b\} = C - \tfrac{1}{2}(y - Ub) N^{-1}(y - Ub)$$

$$\frac{\partial pnL}{\partial b} = +U'N^{-1}U$$

$$J = \delta[U'N^{-1}U] = U'N^{-1}U$$

the covariance is restricted to $$\text{Cov}[B] \geq [U'N^{-1}U]^{-1}$$

For an a priori estimate of J, the expectation operator cannot be dropped; if u is a stochastic signal (n is white noise), then:

$$N^{-1} = \frac{1}{\sigma_n^2} I \text{ and } J = \frac{1}{\sigma_n^2} \delta[U'U],$$

$B = \{B_o, B_1\}$ in case where $U_o$ & $U$, represents the same sequence of samples sifted in time over a single discrete sampling interval $$\partial\{U'U\} = k \begin{bmatrix} \psi uu(0) \psi uu(1) \\ \psi uu(1) \psi uu(0) \end{bmatrix} = k\sigma_u^2 \begin{bmatrix} 1 & p \\ p & 1 \end{bmatrix}$$

the minimum covariance is given by $$\text{cov}[B] = \frac{\sigma_n^2}{k\sigma_u^2} \frac{1}{1-p^2} \begin{bmatrix} 1 & -p \\ -p & 1 \end{bmatrix} = c \begin{bmatrix} 1 & -p \\ -p & 1 \end{bmatrix}$$

for $p \neq o$ the off diagonal expression is equivalent to a correlation between errors $B_o$ & $B_1$, and by means of a sample transformation, it is possible to observe the variance of the vector componnts $T\beta$;

$$T_B = \frac{1}{\sqrt{2}} \begin{bmatrix} 1 & 1 \\ -1 & 1 \end{bmatrix} \begin{bmatrix} B_0 \\ B_1 \end{bmatrix} = \frac{1}{\sqrt{2}} \begin{bmatrix} B_0 + B_1 \\ -B_0 + B_1 \end{bmatrix} = \gamma$$

$$\text{cov}[\gamma] = \frac{c}{2} \begin{bmatrix} 1 & 1 \\ -1 & 1 \end{bmatrix} \begin{bmatrix} 1 & -p \\ -p & 1 \end{bmatrix} \begin{bmatrix} 1 & -1 \\ 1 & 1 \end{bmatrix} = c \begin{bmatrix} 1-p & 0 \\ 0 & 1+p \end{bmatrix}$$

The continuous input of digitized signals is broken down into discrete matrix patterns which are reconverted into a series of overlapping fields, forming a single image of a given quadrant, in accordance with the foregoing. A program incorporating the foregoing controls the operation of the system and method of the invention, whereby the characteristics of laser light employed by the invention are cntrolled to perform the respective functions of non-invasive, non-destructive diagnosis and treatment of aberrant physiological conditions and sites.

In operation, the invention has two modes: diagnostic and surgical. In each of these modes, the system is computer controlled by use of programs based upon the mathematical formulation specified hereinabove.

In the diagnostic mode, doppler analysis of laser radiation relfected or re-emitted from the suspected aberrant target site is employed in order to obtain the chemical composition, molecular weight, concentration, dipole moment (if electrophoresis is used), and other characteristics of the suspected lesion, for purposes of diagnosis thereof.

In the diagnostic mode, the diaphragm 11 is computer controlled by the aforesaid program to perform such functions as aligning the reference beam 9, controlling its radial size, and in some cases involving longer wavelengths, to modulate wave amplitude by direct variation of the apertures of the diaphragm.

The beam splitters 25, 26, 27, 28 are similarly controlled by the aforesaid program to permit selected lines or re-emissions to reverse the reference axis while concurrently deleting or reflecting other lines from the same beam, for purposes of doppler analysis of the selected wavelength or wavelengths. The beam splitters are adapted for such functions by means of the dielectric surface thereon which, in contrast to that of conventional beam splitters, is capable of being electrically charged. This characteristic affords the capability of differential reflection for doppler analysis purposes of beams incident thereon.

The dye cell and rotational mirror complex 29 provides an alternative means for doppler analysis whereby selected wavelengths may be altered either by deletion of spectral lines or by the addition of emissive spectral lines caused by selective bombardment of fluorescent dyes in complex 29, thus producing excitation of such dyes and consequent re-emission of the wavelengths from such dyes, which are circulated through dye cell 30. Electronic characterics with respect to exposure intervals, wavelength modulation, amplitude peak oscillation, are under the control of the electromechanical chopper means 52 and associated systems, which in turn are computer controlled by the aforesaid program. The shutter unit, beam splitter unit, diaphragm unit, and chopper unit have the function of projecting either single or multiple beams along the reference axis, either to or away from the target site (i.e., for purposes of directing the beam to a location where analysis can be conducted) or toward the reference site (i.e., for direction thereon of a laser light beam for purposes of diagnosis or treatment). When the unit is directed toward the target site, the aforesaid elements project the beam so as to impinge upon a turret system mounted on the XYZ translational stage 66. The function of stage 66, which is automated and under the control of the aforesaid program, is to collemate, focus, use or otherwise direct one or more emissive laser beams onto one or more elements of fiber optics array 92. The translational stage 66 operates in conjunction with a plurality of opitically coated compound micro-objectives, 69, 70, 71, 72 or the highly reflective piezoelectric means 73. The micro-objective and piezoelectric elements may function either jointly, sequentially, or simultaneously to direct one or more beams onto the fiber array 92, a portion of which has a terminus forming an emissive fiber optics element of the conduit system 302.

Conduit system 302, as noted hereinabove, constitutes a complex of emissive fiber optics 92, infusion and aspiration flow means 310, 311, and a return self-focusing fiber optics imaging system 288, with the entire conduit system being contained in a hydraulic hypodermic system 299; the latter transports the entire conduit system 302 to a selected site for diagnosis and/or treatment. In connection therewith, infusion and aspiration are accomplished through pump complex 264 which, as previously noted, is computer controlled to maintain ambient temperature, pressure, and chemical integrity of the specified target site for the purposes of efficient operation of the emissive fiber array and to protect the target site itself. As noted, the infusate and aspirate provide an optically emissive curtain from which an emission sequence can effectively be directed upon one or more target sites. The flow of infusate is inspired toward the pump means to provide a continuously flowing barrier for the emissive array and for use in connection with electrophoretic laser analysis.

Optical electronic signals received, which have been reflected or re-emitted from the target site, are received from the optics array 92, in accordance with the aforesaid program, are digitized and collated with other informational data and are used to accomplish laser doppler analysis. The digitized information is arranged in accordance with the aforesaid mathematical scheme into the form of an information matrix which then controls the output of all elements of the system with respect to operation of the emission exposure, wavelength characteristics, and other properties based on electronic spectrum analysis of the aberrant site.

Specific target sites or multiple target sites can be discerned by such techniques as nuclear magnetic resonance, CAT scan, angiography, or other such means in connection with initiating a procedure for diagnosis and correction of undesired pathological conditions. The catheter needle 305 containing the conduit array 302 is positioned adjacent the target site 304. As noted, the conduit contains means for scanning and observing the target site by means of laser telemetry; of course, direct optical observation may also be employed.

Laser telemetry in connection with doppler analysis comprises a form of surgery employing laser light and utilizes three or more separate emissive wave characteristics within a context of dyhetrodyne beaming. The latter provides a means for targeting and homing in on a target site for tracking certain selected parameters, such as specified levels of given blood-borne substances, such as enzymes, hormones, metabolites, or other biochemical compounds on a molecular level. After tracking is accomplished, appropriate intercept vectors are computed by computer system 298 which controls the movement of conduit 302 to provide a stable position from which conduit 302 can address the target site 304.

A low level laser emission then provides information specifying the precise location of the target site with respect to the emissive element. A high energy emission sequence of laser light then excites a localized portion of site 304 and thereby supplies sufficient energy that site 304 undergoes absorptive exhortation and subsequent re-emission of predictable emission spectra. The emission spectra provide data pertaining to the drift and doppler spectrum, the thermal induction gradient, and the translational diffusion. The spectral values are digitized and processed by spectrum analyzer 405, 408 and are then compared to known values by a multichannel analyzer complex 408a.

Magnetic flow devices 279, 280, 281, 282, 314, 315 act in connection with optical electronic devices (not shown) to maintain ambient conditions of pressure and temprature with respect to regions adjacent the target area 304. The net input and outflow of pump means 100', which controls the rate of infusion and aspiration of subconduit structures 312, 313, are controlled by computer 410 based upon input from the aforesaid magnetic flow sensor together with other feedback sensors.

In accordance with the mathematical development disclosed hereinabove, a stochastic search is coupled with variations of the maximum likelihood method to afford a means whereby elements of the system can be adjusted for precise control of electronic wave characteristics, beam intensity exposure intervals, and other selected properties of single or multiple laser emissions for optimally affecting a target site without excessively affecting any region connected thereto or in the periphery thereof.

The foregoing disclosure is a respresentative form of the invention and process and is to be interpreted in an illustrative rather than in a limiting sense. The invention and devised processes are to be accorded the full scope of the claims appended hereto.

What is claimed is:

1. A system for diagnosing and treating aberrant organic sites comprising:
   insertion means for insertion into the body of a subject wherein an aberrant site is located;
   guide means for guiding said insertion means to a position adjacent said aberrant site;
   first optical means in said insertion means for directing laser light to the aberrant site and for receiving from said aberrant site laser light reflected or re-emitted therefrom;

second optical means connected with said first optical means for receiving laser light from said first optical means and directing said light to a selected location and for receiving laser light from a source thereof and directing said laser light to said first optical means, whereby said reflected or re-emitted laser light is analyzable by doppler analysis for diagnosis of said aberrant site and said laser light is directable toward said aberrant site for departicalization thereof;

conduit means connected to said first optical means for providing a flow of optically emissive moderator material and for aspirating said flow in selected directions relative to the transmission axis of said first optical means for supplying a protective barrier between said first optical means and the target site; and said conduit means includes pump means and sensor means, said pump means responding to said sensor means to displace optically opaque physiological materials within the subject wherein said target site is disposed and to replace said optically opaque physiological material with optically emissive infusate material such as to substantially maintain the ambient pressure in the region of said aberrant site and wherein said pump means is controlled to provide negative pressure of aspiration substantially equal to positive pressure of said infusate material, thereby providing a fluid barrier preventing thermal adhesion of unwanted organic constituents to said fiber optic means.

2. The invention as set forth in claim 1 wherein said second optical means includes chopper means operatively connected to said first optical means for controlling the duration of laser light directed to and emanated from said optical means.

3. The invention as set forth in claim 2 wherein said second optical means includes beam splitter means optically alignable with said chopper means for directing selected portions of wavelengths of laser light received from the chopper means toward a desired location for analysis thereof and for diverting other portions of wavelengths of laser light away from said location.

4. The invention as set forth in claim 3 wherein said second optical means further includes diaphragm means optically alignable with said beam splitter means for controlling optical characteristics of light directed to said beam splitter means and emanating from said beam splitter means.

5. The invention as set forth in claim 2 wherein said second optical means further includes color emission means optically alignable with said chopper means, said color emission means comprising means for re-emitting light received from or directed to said chopper means and for changing the wavelength of said light.

6. The invention as set forth in claim 4 wherein said chopper means, said beam splitter means, and said diaphragm means are controlled to provide laser light of selected optical characteristics.

7. The invention as set forth in claim 6 wherein said optical characteristics include intensity, duration, and wavelength.

8. The invention as set forth in claim 5 wherein said chopper means, said color emission means, and said diaphragm means are controlled to provide laser light of selected optical characteristics.

9. The invention as set forth in claim 1 wherein said second optical means further includes directing and focusing means alignable with said first optical means for directing laser light thereto and therefrom.

10. The invention as set forth in claim 1 further including control means for controlling said guide means, said first optical means, and said second optical means to diagnose or treat the suspected aberrant site substantially without damaging adjoining tissue.

11. The invention as set forth in claim 1 wherein said insertion means further includes a catheter needle member and a hypodermic syringe member, said hypodermic syringe member including hydraulic means engageable with said conduit means for moving the latter through said catheter means relative to a selected aberrant site, and further including clamp means having diaphragm means to prevent leakage, said hypodermic syringe means further including a flow member containing a neutral medium for facilitating movement of said conduit means through said catheter member.

12. The invention as set forth in claim 3 wherein said beam splitter means comprises mirror means controllable such that the emissivity thereof may be substantially confined to selected wavelengths of laser light while being substantially totally reflective to other than selected wavelengths of laser light.

13. The invention as set forth in claim 5 wherein said color emission means comprises at least one dye cell containing a selected dye medium, and further comprises at least one pair of spaced apart rotatable wheel members, each one of said at least one pair of rotatable wheel members having mounted thereon a plurality of mirror elements, said mirror elements being partially emissive and partially reflective and having selected spectrocharacteristics, said at least one dye cell being disposed within an optical cavity between said pair of rotatable wheel members, the wheel members being controlled to rotate to a selected setting to present one selected mirror element at a time to said laser light.

14. The invention as set forth in claim 9 wherein said directing and focusing means comprises a turret member mounted on an XYZ translation stage, said turret member including a plurality of lens elements and a piezoelectric element, the turret being controlled and movable on said XYZ translation stage member such that at least one beam of laser light may be directed and focused by one of said lens elements and said piezoelectric, or by either of them.

15. The invention as set forth in claim 12 wherein said mirror means includes a coating of dielectric material which is electrically chargeable to adjust the emissivity and reflectivity with respect to selected wavelengths of laser light.

16. A system for diagnosing and treating aberrant organic sites comprising:

insertion means for insertion into the body of a subject wherein an aberrant site is located;

guide means for guiding said insertion means to a position adjacent said aberrant site;

first optical means in said insertion means for directing laser light to the aberrant site and for receiving from said aberrant site laser light reflected or re-emitted therefrom;

second optical means connected with said first optical means for receiving laser light from said first optical means and directing said light to a selected location and for receiving laser light from a source thereof and directing said laser light to said first optical means, whereby said reflected or re-emitted laser light is analyzable by doppler analysis for diagnosis of said aberrant site and said laser light is directable toward said aberrant site for departicalization thereof;

conduit mans connected to said first optical means for providing a flow of optically emissive moderator material and for aspirating said flow in selected directions relative to the transmission axis of said first optical means for supplying a protective barrier between said first optical means and the target site; and said insertion means further includes a catheter needle member and a hypodermic syringe member, said hypodermic syringe member including hydraulic means engageable with said conduit means for moving the latter through said catheter means relative to a selected aberrant site, and further including clamp means having diaphragm means to prevent leakage, said hypodermic syringe means further including a flow member containing a neutral medium for facilitating movement of said conduit means through said catheter member.

17. The invention as set forth in claim 16 wherein said second optical means includes chopper means operatively connected to said first optical means for controlling the duration of laser light directed to and emanated from said optical means.

18. The invention as set forth in claim 17 wherein said second optical means includes beam splitter means optically alignable with said chopper means for directing selected portions of wavelengths of laser light received from the chopper means toward a desired location for analysis thereof and for diverting other portions of wavelengths of laser light away from said location.

19. The invention as set forth in claim 16 wherein said second optical means further includes diaphragm means optically alignable with said beam splitter for controlling optical characteristics of light directed to said beam splitter means and emanating from said beam splitter means.

20. The invention as set forth in claim 19 wherein said second optical means further includes color emission means optically alignable with said chopper means, said color emission means compromising means for re-emitting light received from or directed to said chopper means and for changing the wavelengths of said light.

21. The invention as set forth in claim 19 wherein said chopper means, said beam splitter means, and said diaphragm means are controlled to provide laser light of selected optical characteristics.

22. The invention as set forth in claim 21 wherein said optical characteristics include intensity, duration, and wavelength.

23. The invention as set forth in claim 19 wherein said chopper means, said color emission means, and said diaphragm means are controlled to provide laser light of selected optical characteristics.

24. The invention as set forth in claim 16 wherein said second optical means further includes directing and focusing means alignable with said first optical means for directing laser light thereto and therefrom.

25. The invention as set forth in claim 16 further including control means for controlling said first guide means, said first optical means, and said second optical means to diagnose or treat the suspected aberrant site substantially without damaging adjoining tissue.

26. The invention as set forth in claim 19 wherein said beam splitter means comprises mirror means controllable such that the emissivity thereof may be substantially confined to selected wavelengths of laser light while being substantially totally reflective to other than selected wavelengths of laser light.

27. The invention as set forth in claim 20 wherein said color emission means comprises at least one dye cell containing a selected dye medium, and further comprises at least one pair of spaced apart rotatable wheel members, each one of said at least one pair of rotatable wheel members having mounted thereon a plurality of mirror elements, said mirror elements being partially emissive and partially reflective and having selected spectrocharacteristics, said at least one dye cell being disposed within an optical cavity between said pair of rotatable wheel members, the wheel members being controlled to rotate to a selected setting to present one selected mirror element at a time to said laser light.

28. The invention as set forth in claim 24 wherein said directing and focusing means comprises a turret member mounted on an XYZ translation stage, said turret member including a plurality of lens elements and a piezoelectric element, the turret being controlled and movable on said XYZ translation stage member such that at least one beam of laser light may be directed and focused by one of said lens elements and said piezoelectric, or by either of them.

29. The invention as set forth in claim 26 wherein said mirror means includes a coating of dielectric material which is electrically chargable to adjust the emissivity and reflectivity with respect to selected wavelengths of laser light.

30. A system for diagnosing and treating aberrant organic sites comprising:

insertion means for insertion into the body of a subject wherein an aberrant site is located;

guide means for guiding said insertion means to a position adjacent said aberrant site;

first optical means in said insertion means for directing laser light to the aberrant site and for receiving from said aberrant site laser light reflected or re-emitted therefrom;

second optical means connected with said first optical means for receiving laser light from said first optical means and directing said light to a selected location and for receiving laser light from a source thereof and directing said laser light to said first optical means, whereby said reflected or re-emitted laser light is analyzable by doppler analysis for diagnosis of said aberrant site and said laser light is directable toward said aberrant site for departicalization thereof;

said second optical means further includes directing and focusing means alignable with said first optical means for directing laser light thereto and therefrom; and said directing and focusing means comprises a turret member mounted on an XYZ translation stage, said turret member including a plurality of lens elements and a piezoelectric element, the turret being controlled and movable on said XYZ translation stage member such that at least one beam of laser light may be directed and focused by one of said lens elements and said piezoelectric, or by either of them.

31. The invention as set forth in claim 30 wherein said second optical means includes chopper means operatively connected to said first optical means for controlling the duration of laser light directed to and emanated from said optical means.

32. The invention as set forth in claim 31 wherein said second optical means includes beam splitter means optically alignable with said chopper means for directing selected portions of wavelengths of laser light received from the chopper means toward a desired location for analysis thereof and for diverting other portions of wavelengths of laser light away from said location.

33. The invention as set forth in claim 30 wherein said second optical means further includes diaphragm means optically alignable with said beam splitter means for controlling optical characteristics of light directed to said beam splitter means and emanating from said beam splitter means.

34. The invention as set forth in claim 33 wherein said second optical means further includes color emission means optically alignable with said chopper means, said color emission means comprising means for re-emitting light received from or directed to said chopper and for changing the wavelength of said light.

35. The invention as set forth in claim 33 wherein said chopper means, said beam splitter means, and said diaphragm means are controlled to provide laser light of selected optical characteristics.

36. The invention as set forth in claim 35 wherein said optical characteristics include intensity, duration, and wavelength.

37. The invention as set forth in claim 34 wherein said chopper means, said color emission means, and said diaphragm means are controlled to provide laser light of selected optical characteristics.

38. The invention as set forth in claim 30 further including control means for controlling said first guide means, said first optical means, and said second optical means to diagnose or treat the suspected aberrant site substantially without damaging adjoining tissue.

39. The invention as set forth in claim 30 further including conduit means connected to said first optical means for providing a flow of optically emissive moderator material and for aspirating said flow in selected directions relative to the transmission axis of said first optical means for supplying a protective barrier between said first optical means and the target site.

40. The invention as set forth in claim 31 wherein said beam splitter means comprises mirror means controllable such that the emissivity thereof may be substantially confined to selected wavelengths of laser light while being substantially totally reflective to other than selected wavelengths of laser light.

41. The invention as set forth in claim 34 wherein said color emission means comprises at least one dye cell containing a selected dye medium, and further comprises at least one pair of spaced apart rotatable wheel members, each one of said at least one pair of rotatable wheel members having mounted thereon a plurality of mirror elements, said mirror elements being partially emissive and partially reflective and having selected spectrocharacteristics, said at least one dye cell being disposed within an optical cavity between said pair of rotatable wheel members, the wheel members being controlled to rotate to a selected setting to present one selected mirror element at a time to said laser light.

42. The invention as set forth in claim 40 wherein said mirror means includes a coating of dielectric material which is electrically chargeable to adjust the emissivity and reflectivity with respect to selected wavelengths of laser light.

* * * * *